US009392796B2

(12) United States Patent
Thompson et al.

(10) Patent No.: US 9,392,796 B2
(45) Date of Patent: Jul. 19, 2016

(54) PLANT GROWTH-PROMOTING BACTERIA AND METHODS OF USE

(71) Applicant: Spogen Biotech Inc., Columbia, MO (US)

(72) Inventors: Brian Thompson, Columbia, MO (US); Katie Thompson, Columbia, MO (US); Brittany Angle, Columbia, MO (US)

(73) Assignee: Spogen Biotech Inc., St. Louis, MO (US)

( * ) Notice: Subject to any disclaimer, the term of this patent is extended or adjusted under 35 U.S.C. 154(b) by 0 days.

(21) Appl. No.: 14/213,238

(22) Filed: Mar. 14, 2014

(65) Prior Publication Data

US 2014/0274691 A1 Sep. 18, 2014

Related U.S. Application Data

(60) Provisional application No. 61/790,476, filed on Mar. 15, 2013.

(51) Int. Cl.
| | |
|---|---|
| *C12N 1/20* | (2006.01) |
| *C12N 1/32* | (2006.01) |
| *C12N 1/38* | (2006.01) |
| *A01N 63/00* | (2006.01) |
| *A01H 3/00* | (2006.01) |
| *C07K 14/195* | (2006.01) |
| *C07K 14/21* | (2006.01) |

(52) U.S. Cl.
CPC . *A01N 63/00* (2013.01); *A01H 3/00* (2013.01)

(58) Field of Classification Search
USPC ............ 435/834, 252.1, 254.1, 256.5, 253.5, 435/320.1, 69.1, 6.15, 6.18, 244, 252.4, 435/252.5; 504/100; 536/23.1; 424/93.46
IPC .. A01N 63/00,63/02, 47/28; C05F 11/08; Y10S 435/864; A01H 5/00; C07K 14/21, 14/195; C12N 1/20, 1/38, 1/32; C12R 1/11
See application file for complete search history.

(56) References Cited

U.S. PATENT DOCUMENTS

| 5,503,652 A | 4/1996 | Kloepper et al. |
| 6,309,440 B1 | 10/2001 | Yamashita |
| 7,393,678 B2 | 7/2008 | Triplett et al. |
| 2003/0228679 A1 | 12/2003 | Smith et al. |

FOREIGN PATENT DOCUMENTS

| CN | 10-2031231 A | 4/2011 |
| EP | 1 465 980 B1 | 8/2010 |
| IN | 801/CHE/2011 | 7/2014 |
| WO | 02/45513 A2 | 6/2002 |
| WO | 2009/056494 A2 | 5/2009 |
| WO | 2013090628 | * 6/2013 |

OTHER PUBLICATIONS

Prusty et al. 2004. The plant hormone indoleacetic acid induces invasive growth in *Saccharomyces cerevisiae*. PNAS, vol. 101, No. 12, pp. 4153-4157.*
Leveau et al., 2005. Utilization of the Plant Hormone Indole-3-Acetic Acid for Growth by Pseudomonas putida Strain 1290. Applied and Environmental Microbiology, vol. 71, No. 5, pp. 2365-2371.*
Pereira. 2010. Compatibility among fungicide treatments on soybean seeds through film coating and inoculation with Bradyrhizobium strains—doi: 0.4025/actasciagron.v32i4.5756.*
Pereira, Carlos Eduardo et al., "Compatibility among fungicide treatments on soybean seeds through film coating and inoculation with Bradyrhizobium strains", Acta Scientarium. Agronomy, Maringá, v. 32, n. 4, p. 585-589, 2010.
Yadav, S., et al., "Diversity and Phylogeny of Plant Growth-Promoting Bacilli from Moderately Acidic Soil," Journal of Basic Microbiology, Feb. 2011, pp. 98-106, vol. 51, No. 1.
Yegorenkova, I. V., et al., "Paenibacillus polymyxa Rhizobacteria and Their Synthesized Exoglycans in Interaction With Wheat Roots: Colonization and Root Hair Deformation," Current Microbiology, 2013, pp. 481-486, vol. 66, No. 5.
Zou, C., et al., "Bacillus megaterium Strain XTBG34 Promotes Pant Growth by Producing 2-pentylfuran," Journal of Microbiology, Aug. 2010, pp. 460-466, vol. 48, No. 4.
Anand, R., et al., "N2-Fixation and Seedling Growth Promotion of Lodgepole Pine by Endophytic Paerilbacillus polymyxa," Microbial Ecology, 2013, pp. 369-374, vol. 66, No. 2.
Bent, E., et al., "Alterations in Plant Growth and in Root Hormone Levels of Lodgepole Pines Inoculated with Rhizobacteria," Canadian Journal of Microbiology, Sep. 2001, pp. 793-800, vol. 47, No. 9.
Chakraborty, U., et al., "Plant Growth Promotion and Induction of Resistance in Camellia sinensis by Bacillus megaterium," Journal of Basic Microbiology, 2006, pp. 166-195, vol. 46, No. 3.
Da Mota, F. F., et al., "Auxin Production and Detection of the Gene Coding for the Auxin Efflux Carrier (AEC) Protein in Paenibacillus polymyxa," Journal of Microbiology, Jun. 2008, pp. 257-264, vol. 46, No. 3.
Ding, Y., et al., "Isolation and Identification of Nitrogen-Fixing Bacilli from Plant Rhizospheres in Beijing Region" Journal of Applied Microbiology, 2005, pp. 1271-1281, vol. 99, No. 5.
Doronina, N. V., et al. , "Emended Description of Paracoccus kondratievae," International Journal of Systematic and Evolutionary Microbiology, Mar. 2002, pp. 679-682, vol. 52, Part 2.
English, M. M., et al., "Overexpression of hns in the Plant Growth-Promoting Bacterium Enterobacter cloacae UW5 Increases Root Colonization," Journal of Applied Microbiology, 2009, pp. 2180-2190, vol. 108, No. 6.
Erturk, Y., et al., "Effects of Plant Growth Promoting Rhizobacteria (PGPR) on Rooting and Root Growth of Kiwifruit (*Actinidia deliciosa*) Stem Cuttings," Biological Research, 2010, pp. 91-98, vol. 43, No. 1.
Faria, D. C., et al., "Endophytic Bacteria Isolated From Orchid and Their Potential to Promote Plant Growth " World Journal of Microbiology & Biotechnology, 2013, pp. 217-221, vol. 29, No. 2.

(Continued)

*Primary Examiner* — Debbie K Ware
*Assistant Examiner* — Kailash C Srivastava
(74) *Attorney, Agent, or Firm* — Senniger Powers LLP

(57) ABSTRACT

The present invention generally relates to bacteriologically pure bacterial cultures of novel strains of plant growth-promoting bacteria, and inoculums comprising the same. The invention is also directed to plant seeds coated with the inoculums, kits comprising the inoculums and methods for stimulating plant growth by applying the biologically pure bacterial culture or the inoculum to a plant, plant seed, or plant growth medium.

19 Claims, No Drawings

(56) References Cited

OTHER PUBLICATIONS

Forage, R. G., et al., "Glycerol Fermentation in Klebsiella pneumoniae. Functions of the Coenzyme B12-Dependent Glycerol and Diol Dehydratases," Journal of Bacteriology, Feb. 1982, pp. 413-419, vol. 149, No. 2.

Haggag, W. M., et al., "Colonization of Peanut Roots by Biofilm-Forming Paenibacillus polymyxa Initiates Biocontrol Against Crown Rot Disease," Journal of Applied Microbiology, 2008, pp. 961-969, vol. 104, No. 4.

Hinton, D. M., et al., "Enterobacter cloacae is an Endophytic Symbiont of Corn," Mycopathologia, 1995, pp. 117-125, vol. 129, No. 2.

Hontzeas, N., et al., "Changes in Gene Expression in Canola Roots Induced by ACC-Deaminase-Containing Plant-Growth-Promoting Bacteria," Molecular Plant-Microbe interactions, Aug. 2004, pp. 865-871, vol. 17, No. 8.

Iniguez, A. L., et al., "Nitrogen Fixation in Wheat Provided by Klebsiella pneumoniae 342," Molecular Plant-Microbe Interactions, Oct. 2004, pp. 1078-1085, vol. 17, No. 10.

International Search Report and Written Opinion issued for PCT/US2014/030726, issued on Aug. 19, 2014, 13 pages.

Islam, M. R., et al., "Characterization of Plant Growth-Promoting Traits of Free-Living Diazotrophic Bacteria and Their Inoculation Effects on Growth and Nitrogen Uptake of Crop Plants," Journal of Microbiology and Biotechnology, Oct. 2009, pp. 1213-1222, vol. 19, No. 10.

Jeong, H., et al., "Draft Genome Sequence of the Paenilbacillus polymyxa Type Strain (ATCC 8421), A Plant Growth-Promoting Bacterium," Journal of Bacteriology, 2011, pp. 5026-5027, vol. 193, No. 18.

Karakurt, H., et al., "Effects of Indol-3-butyric Acid (IBA), Plant Growth Promoting Rhizobacteria (PGPR) and Carbohydrates on Rooting of Hardwood Cutting of MM106 Apple Rootstock," African Journal of Agricultural Research, Feb. 2009, pp. 060-064, vol. 4, No. 2.

Khan. Z., et al., "A Plant Growth Promoting Rhizobacterium, Paenibacillus polymyxa Strain GBR-1, Suppresses Root-Knot Nematode," Technology, May 2008, pp. 3016-3023, vol. 99, No. 8.

Kim, J. F., et al., "Genome Sequence of the Polymyxin-Producing Plant-Probiotic Rhzobacttenum Paenibacillus polymyxa E681," Journal of Bacteriology, 2010, pp. 6103-6104, vol. 192, No. 22.

Kishore, G. K. et al., "Phylioplane Bacteria Increase Seedling Emergence, Growth and Yield of Field-Grown Groundnut (*Arachis hypogaea* L.)," Letters in Applied Microbiology, 2005, pp. 260-268, vol. 40, No. 4.

Lamsal, K., et al., "Application of Rhizobacteria for Plant Growth Promotion Effect and Biocontrol of Anthracnose Caused by Colletotrichurn acutatum on Pepper," Mycobiology, Dec. 2012, pp. 244-251, vol. 40, No. 4.

Lee, S., et al., "Growth Promotion of Xanthium italicum by Application of Rhizobacterial Isolates of Bacillus aryabhattai in Microcosm Soil," Journal of Microbiology, Feb. 2012, pp. 45-49, vol. 50, No. 1.

Leite, H. A., et al., "Bacillus subtilis and Enterobacter cloacae Endophytes From Healthy *Theobroma cacao* L. Trees can Systemically Colonize Seedlings and Promote Growth," Applied Microbiology and Biotechnology, Dec. 2012, pp. 2639-2651, vol. 97, No. 6.

Li, J., et al., "An ACC Deaminase Minus Mutant of Enterobacter cloacae UW4 No Longer Promotes Root Elongation," Current Microbiology, Aug. 2000, pp. 101-105, vol. 41, No. 2.

Liu, X., et al., "Colonization of Maize and Rice Plants by Strain Bacillus megaterium C4," Current Microbiology. 2006, pp. 186-190, vol. 52, No. 3.

Liu, Y., et al., "Study on Mechanisms of Colonization of Nitrogen-Fixing PGPB, Klebsiella pneurnoniae NG14 on the Root Surface of Rice and the Formation of Biofilm," Current Microbiology, 2011, pp. 1113-1122, vol. 62, No. 4.

Lopez-Bucio, J., et al., "Bacillus megaterium Rhizobacteria Promote Growth and Alter Root-System Architecture Through an Auxin- and Ethylene-Independent Signaling Mechanism in Arahidopsis thaliana," Molecular Plant-Microbe Interactions, Feb. 2007, pp. 207-217, vol. 20, No. 2.

Madmony, A., et al., "Enterobacter cloacae, An Obligatory Endophyte of Pollen Grains of Mediterranean Pines," Folia Microbioiogica (Praha), 2005, pp. 209-216, vol. 50, No. 3.

Maes, M., et al., "Experiences and Perspectives for the Use of a Paenibacillus Strain as A Plant Protectant " Communications in Agricultural and Applied Biological Sciences, 2003, pp. 457-462, vol. 68, No. 4, Part B.

Marulanda, A., et al., "Regulation of Plasma Membrane Aguaporins by Inoculation with a Bacillus megaterium Strain in Maize (*Zea mays* L.) Plants Under Unstressed and Salt-Stressed Conditions," Planta, 2010, pp. 533-543, vol. 232, No. 2.

Meldau, D. G., et al., "A Native Plant Growth Promoting Bacterium, Bacillus sp. B55, Rescues Growth Performance of an Ethylene-Insensitive Plant Genotype in Nature," Frontiers in Plant Science, Jun. 2012, pp. 1-13, vol. 3, Article 112.

Ortiz-Castro, R., et al., "Plant Growth Promotion by Bacillus megaterium Involves Cytokinin Signaling," Plant Signaling & Behavior, Apr. 2008, pp. 263-265, vol. 3, No. 4.

Penrose, D. M., et al., "Levels of ACC and Related Comounds in Exudate and Extracts of Canola Seeds Treated with ACC Deaminase-Containing Plant Growth-Promoting Bacteria," Canadian Journal of Microbiology, Apr. 2001, pp. 368-372, vol. 47, No. 4.

Petrov, K., et al., "High Production of 2.3-butanediol From Glycerol by Klebsiella pneumoniae G31," Applied Microbioiogy and Biotechnology, 2009, pp. 659-665, vol. 84, No. 4.

Phi, Q. T., et al., "Assessment of Root-Associated Paenibacillus polymyxa Groups on Growth Promotion and Induced Systemic Resistance in Pepper," Journal of Microbiology and Biotechnology, Dec. 2010, pp. 1605-1613, vol. 20, No. 12.

Rajendran, G., et al., "Enhanced Growth and Nodulation of Pigeon Pea by Co-Inoculation of Bacillus Strains with Rhizobium spp," Bioresource Technology, 2007, pp. 4544-4550, vol. 99, No. 11.

Rajkumar, M., et al., "Effects of Inoculation of Plant-Growth Promoting Bacteria on Ni Uptake by Indian Mustard," Bioresource Technology, 2008, pp. 3491-3498, vol. 99, No. 9.

Ryu, C. M., et al., "Bacterial Volatiles Promote Growth in Arabidopsis," Proceedings of the National Academy of Sciences of the United States of America, Apr. 2003, pp. 4927-4932, vol. 100, No. 8.

Sachdev, D. P., et al., "Isolation and Characterization of Indole Acetic Acid (IAA) Producing Klebsiella pneumoniae Strains from Rhizosphere of Wheat (*Triticum aestivum*) and Their Effect on Plant Growth" Indian Journal of Experimental Biology, Dec. 2009, pp. 993-1000, vol. 47, No. 12.

Saleh, S. S., et al., "Involvement of gacS and rpoS in Enhancement of the Plant Growth-Promoting Capabilities of Enterobacter cloacae CAL2 and UW4," Canadian Journal of Microbiology, Aug. 2001, pp. 698-705, vol. 47, No. 8.

Shahid, M., et al., "Root Colonization and Growth Promotion of Sunflower (*Helianthus arinuus* L.) by Phosphate Solubilizing Enterobacter sp. Fs-11," World Journal of Microbiology & Biotechnology, 2012, pp. 2749-2758, vol. 28, No. 8.

Shankar, M., et al., "Root Colonization of a Rice Growth Promoting Strain of Enterobacter cloacae," Journal of Basic Microbiology, 2011, pp. 523-530, vol. 51, No. 5.

Thomas, P., et al., "Endophytic Bacteria Associated with Growing Shoot Tips of Banana (*Musa* sp.) cv. Grand Naine and the Affinity of Endopinytes to the Host," Microbial Ecology, 2009, pp. 952-984, vol. 58, No. 4.

Timmusk, S., et al., "The Plant-Growth-Promoting Rhizobacterium Paenibacillus polymyxa Induces Changes in Arabidopsis thaliana Gene Expression: A Possible Connection Between Biotic and Abiotic Stress Responses," Molecular Plant-Microbe Interactions, Nov. 1999, pp. 951-959. vol. 12, No. 11.

(56) References Cited

OTHER PUBLICATIONS

Timmusk, S., et al., "Paenibacillus polymyxa Invades Plant Roots and forms Biofilms," Applied and Environmental Microbiology, Nov. 2005, pp. 7292-7300, vol. 71, No. 11.

Trivedi, P., et al., "Plant Growth Promotion Abilities and Formulation of Bacillus megaterium Strain B 388 (MTCC6521) Isolated From a Temperate Himalayan Location," Indian Journal of Microbiology. 2008, pp. 42-347, vol. 48, No. 3.

Vendan, R. T., et al., "Diversity of Endophytic Bacteria in Ginseng and Their Potential for Plant Growth Promotion," Journal of Microbiology, 2010, pp. 559-565, vol. 48, No. 5.

Von Der Weid, I., et al., "Diversity of Paenibacillus polymyxa Strains Isolated From the Rhizosphere of Maize Planted in Cerrado Soil," Research in Microbiology, Jun. 2000, pp. 369-381, vol. 151, No. 5.

Walker, R., et al., "Colonization of the Developing Rhizosphere of Sugar Beet Seedlings by Potential Biocontrol Agents Applied as Seed Treatments," Journal of Applied Microbiology, 2002, pp. 228-237, vol. 92, No. 2.

* cited by examiner

PLANT GROWTH-PROMOTING BACTERIA AND METHODS OF USE

CROSS-REFERENCED TO RELATED APPLICATIONS

This application claims the benefit of U.S. Provisional Patent Application Ser. No. 61/790,476, filed Mar. 15, 2013, the entirety of which is herein incorporated by reference.

FIELD OF THE INVENTION

The present invention generally relates to bacteriologically pure bacterial cultures of novel strains of plant growth-promoting bacteria, and inoculums comprising the same. The invention is also directed to plant seeds coated with the inoculums, kits comprising the inoculums and methods for stimulating plant growth by using the claimed bacterial cultures and/or inoculums.

BACKGROUND OF THE INVENTION

Plant growth-promoting bacteria (PGPB) are associated with many, if not all, plant species and are commonly present in many environments. The most widely studied group of PGPB is plant growth-promoting rhizobacteria (PGPR), which colonize the root surfaces and the closely adhering soil interface, the rhizosphere. Inside the rhizosphere is a zone where bacteria, fungi, and other organisms compete for nutrients and for binding to the root structures of the plant. Both detrimental and beneficial bacteria can occupy the plant's roots. The presence of plant growth-promoting bacteria (PGPB) within or near the roots or seeds can lead to a healthier rhizosphere environment and healthier plants. These free living bacteria promote plant growth in agricultural crops and lead to increased growth and yield at harvest. The bacteria that colonize the roots and maintain their benefits throughout the growth cycle of the plant are especially desired for application during early growth or as a seed coating agent to agricultural crops.

The mechanisms that PGPBs use in promoting plant growth are diverse and often plant- or cultivar-specific. Several PGPB growth-promoting mechanisms are known, which can influence the plant in a direct or indirect manner. The direct mechanism involves increasing plant growth by supplying the plant with nutrients and hormones, such as by fixing nitrogen that is available to plants, synthesizing phytohormones, and providing nutrients such as phosphate to the plant. The indirect mechanism of action for PGPB occurs through the ability to control detrimental fungal and bacterial pathogens from establishing or surviving within the rhizosphere. This is usually achieved through the beneficial secretion of antifungals and other antibiotics by the PGPB. As an additional advantage, PGPBs can also lead to extensive remodeling of the plant root systems.

In recent years, a significant effort has been expanded to identify novel strains of plant growth-promoting bacteria, and use them to promote plant growth, thereby increasing the yield of plant product, reducing the use and amounts of fertilizers and herbicides, and providing other benefits for agricultural and horticultural communities.

SUMMARY OF THE INVENTION

In one aspect, the present invention is directed to a biologically pure bacterial culture wherein the bacteria in the bacterial culture is: (a) *Bacillus aryabhattai* strain CAP53 (NRRL No. B-50819); (b) *Bacillus aryabhattai* strain CAP56 (NRRL No. B-50817); (c) *Bacillus flexus* strain BT054 (NRRL No. B-50816v); (d) *Paracoccus kondratievae* strain NC35 (NRRL No. B-50820); (e) *Enterobacter cloacae* strain CAP12 (NRRL No. B-50822); or (f) *Bacillus nealsonii* strain BOBA57 (NRRL No. B-50821). Also provided are biologically pure bacterial cultures wherein bacteria in the bacterial cultures are mutants of any of the foregoing strains comprising one or more mutations which retain the ability to promote plant growth.

The present invention is also directed to an inoculum for application to plants, plant seeds, or a plant growth medium, wherein the inoculum comprises an effective amount of a biologically pure bacterial culture disclosed herein and an agriculturally acceptable carrier.

Yet another aspect of the present invention is a method for stimulating plant growth by applying the biologically pure bacterial culture or the inoculum as disclosed herein to a plant, plant seed, or plant growth medium.

The present invention also provides a method for stimulating plant growth by applying glycerol, pyruvate, yeast extract, polyol, or a combination thereof to a plant growth medium, and applying at least one bacterial culture or at least one inoculum to a plant or plant seed in the plant growth medium, or to the plant growth medium, wherein the at least one bacterial culture or at least one inoculum is capable of stimulating plant growth.

Another aspect of the present invention is a provision of a plant seed coated with the inoculum or with the bacterial culture disclosed herein.

Yet another aspect of the present invention is a kit for stimulating plant growth comprising an inoculum disclosed herein and instructions for applying the inoculum to plants, plant seeds, or a plant growth medium.

Other objects and features will be in part apparent and in part pointed out hereinafter.

DEFINITIONS

A "biologically pure bacterial culture" refers to a culture of bacteria containing no other bacterial species in quantities sufficient to interfere with the replication of the culture or be detected by normal bacteriological techniques. Stated another way, it is a culture wherein virtually all of the bacterial cells present are of the selected strain.

The term "rhizosphere" is used interchangeably with "root zone" to denote that segment of the soil that surrounds the roots of a plant and is influenced by them.

The term "inoculant" as described in this invention is defined in several Federal, or State regulations as (1) "soil or plant inoculants shall include any carrier or culture of a specific micro-organism or mixture of micro-organisms represented to improve the soil or the growth, quality, or yield of plants, and shall also include any seed or fertilizer represented to be inoculated with such a culture" (New York State 10-A Consolidated Law); (2) "substances other than fertilizers, manufactured, sold or represented for use in the improvement of the physical condition of the soil or to aid plant growth or crop yields" (Canada Fertilizers Act); (3) "a formulation containing pure or predetermined mixtures of living bacteria, fungi or virus particles for the treatment of seed, seedlings or other plant propagation material for the purpose of enhancing the growth capabilities or disease resistance or otherwise altering the properties of the eventual plants or crop" (Ad hoc European Working Group, 1997) or (4) "meaning any chemical or biological substance of mixture of substances or device distributed in this state to be applied to soil, plants or seeds for soil corrective purposes; or which is intended to improve germination, growth, quality, yield, product quality, reproduction, flavor, or other desirable characteristics of plants or which is intended to produce any chemical, biochemical, biological or physical change in soil" (Section 14513 of the California Food and Agriculture Code).

The term "effective amount" refers to a quantity which is sufficient to result in a statistically significant increase of growth and/or of protein yield and/or of grain yield of a plant as compared to the growth, protein yield and grain yield of the control-treated plant.

The terms "agriculturally acceptable carrier" and "carrier" are used interchangeably herein.

The terms "promoting plant growth" and "stimulating plant growth" are used interchangeably herein, and refer to the ability to enhance or increase at least one of the plant's height, weight, leaf size, root size, or stem size, to increase protein yield from the plant or to increase grain yield of the plant.

DETAILED DESCRIPTION

The present invention relates to biologically pure bacterial cultures of plant growth-promoting bacteria (PGPB) wherein the bacteria, i.e. the bacterial strain in each of the bacterial cultures, are selected from the group consisting of *Bacillus aryabhattai* strain CAP53 (NRRL No. B-50819), *Bacillus aryabhattai* strain CAP56 (NRRL No. B-50817), *Bacillus flexus* strain BT054 (NRRL No. B-50816v), *Paracoccus kondratievae* strain NC35 (NRRL No. B-50820), *Enterobacter cloacae* strain CAP12 (NRRL No. B-50822), and *Bacillus nealsonii* strain BOBA57 (NRRL No. B-50821). The foregoing strains were deposited with the United States Department of Agriculture (USDA) Agricultural Research Service (ARS), having the address 1815 North University Street, Peoria, Ill. 61604 U.S.A., on Mar. 11, 2013, and are identified by the NRRL numbers provided in parentheses.

As shown in the Examples, the present strains were isolated from rhizospheres of various vigorous plants, and were shown to be most promising among a large number of isolates by in vitro culturing and application to plants. The novel strains disclosed herein were identified by 16S RNA sequencing and biochemical assays. Thus, *Bacillus aryabhattai* strain CAP53 has a 16S ribosomal RNA sequence having at least about 98%, at least about 99%, or 100% sequence identity with the sequence of SEQ ID NO: 1; *Bacillus aryabhattai* strain CAP56 has a 16S ribosomal RNA sequence having at least about 98%, at least about 99%, or 100% sequence identity with the sequence of SEQ ID NO: 2; *Bacillus flexus* strain BT054 has a 16S ribosomal RNA sequence having at least about 98%, at least about 99%, or 100% sequence identity with the sequence of SEQ ID NO: 3; *Paracoccus kondratievae* strain NC35 has a 16S ribosomal RNA sequence having at least about 98%, at least about 99%, or 100% sequence identity with the sequence of SEQ ID NO: 4; *Enterobacter cloacae* strain CAP12 has a 16S ribosomal RNA sequence having at least about 98%, at least about 99%, or 100% sequence identity with the sequence of SEQ ID NO: 5; and *Bacillus nealsonii* strain BOBA57 has a 16S ribosomal RNA sequence having at least about 98%, at least about 99%, or 100% sequence identity with the sequence of SEQ ID NO: 6. These sequences are shown in Table 1 below.

TABLE 1

| Strain (SEQ ID. NO) | Partial 16S ribosomal RNA sequence |
|---|---|
| *Bacillus aryabhattai* CAP53 (SEQ ID NO: 1) | GGNNCAACGCCGCGTGAGTGATGAAGGCTTTCGGGTC GTAAAACTCTGTTGTTAGGGAAGAACAAGTACGAGAG TAACTGCTCGTACCTTGACGGTACCTAACCAGAAAGC CACGGCTAACTACGTGCCAGCAGCCGCGGTAATACGT AGGTGGCAAGCGTTATCCGGAATTATTGGGCGTAAAG CGCGCGCAGGCGGTTTCTTAAGTCTGATGTGAAAGCC CACGGCTCAACCGTGGAGGGTCATTGGAAACTGGGGA ACTTGAGTGCAGAAGAGAAAAGCGGAATTCCACGTGT AGCGGTGAAATGCGTAGAGATGTGGAGGAACACCAGT GGCGAAGGCGGCTTTTTGGTCTGTAACTGACGCTGAG GCGCGAAAGCGTGGGGAGCAAACAGGATTAGATACCC TGGTAGTCCACGCCGTAAACGATGAGTGCTAAGTGTT AGAGGGTTTCCGCCCTTTAGTGCTGCAGCTAACGCAT TAAGCACTCCGCCTGGGGAGTACGGTCGCAAGACTGA AACTCAAAGGAATTGACGGGGGCCCGCACAAGCGGTG GAGCATGTGGTTTAATTCGAAGCAACGCGAAGAACCT TACCAGGTCTTGACATCCTCTGACAACTCTAGAGATA GAGCGTTCCCCTTCGGGGGACAGAGTGACAGGTGGTG CATGGTTGTCGTCAGCTCGTGTCGTGAGATGTTGGGT TAAGTCCCGCAACG |
| *Bacillus aryabhattai* CAP56 (SEQ ID NO: 2) | TCTGANGGNNCACGCCGCGTGAGTGATGAAGGCTTTC GGGTCGTAAAACTCTGTTGTTAGGGAAGAACAAGTAC GAGAGTAACTGCTCGTACCTTGACGGTACCTAACCAG AAAGCCACGGCTAACTACGTGCCAGCAGCCGCGGTAA TACGTAGGTGGCAAGCGTTATCCGGAATTATTGGGCG TAAAGCGCGCGCAGGCGGTTTCTTAAGTCTGATGTGA AAGCCCACGGCTCAACCGTGGAGGGTCATTGGAAACT GGGGAACTTGAGTGCAGAAGAGAAAAGCGGAATTCCA CGTGTAGCGGTGAAATGCGTAGAGATGTGGAGGAACA CCAGTGGCGAAGGCGGCTTTTTGGTCTGTAACTGACG CTGAGGCGCGAAAGCGTGGGGAGCAAACAGGATTAGA TACCCTGGTAGTCCACGCCGTAAACGATGAGTGCTAA GTGTTAGAGGGTTTCCGCCCTTTAGTGCTGCAGCTAA CGCATTAAGCACTCCGCCTGGGGAGTACGGTCGCAAG ACTGAAACTCAAAGGAATTGACGGGGGCCCGCACAAG CGGTGGAGCATGTGGTTTAATTCGAAGCAACGCGAAG AACCTTACCAGGTCTTGACATCCTCTGACAACTCTAG AGATAGAGCGTTCCCCTTCGGGGGACAGAGTGACAGG TGGTGCATGGTTGTCGTCAGCTCGTGTCGTGAGATGT TGGGTTAAGTCCCGC |
| *Bacillus flexus* BT054 (SEQ ID NO: 3) | GGANCAACGCCGCGTGAGTGANGAAGGCTTTCGGGTC GTAAAACTCTGTTGTTAGGGAAGAACAAGTACAAGAG TAACTGCTTGTACCTTGACGGTACCTAACCAGAAAGC CACGGCTAACTACGTGCCAGCAGCCGCGGTAATACGT AGGTGGCAAGCGTTATCCGGAATTATTGGGCGTAAAG CGCGCGCAGGCGGTTTCTTAAGTCTGATGTGAAAGCC CACGGCTCAACCGTGGAGGGTCATTGGAAACTGGGGA ACTTGAGTGCAGAAGAGAAAAGCGGAATTCCACGTGT AGCGGTGAAATGCGTAGAGATGTGGAGGAACACCAGT GGCGAAGGCGGCTTTTTGGTCTGTAACTGACGCTGAG GCGCGAAAGCGTGGGGAGCAAACAGGATTAGATACCC TGGTAGTCCACGCCGTAAACGATGAGTGCTAAGTGTT AGAGGGTTTCCGCCCTTTAGTGCTGCAGCTAACGCAT TAAGCACTCCGCCTGGGGAGTACGGTCGCAAGACTGA AACTCAAAGGAATTGACGGGGGCCCGCACAAGCGGTG GAGCATGTGGTTTAATTCGAAGCAACGCGAAGAACCT TACCAGGTCTTGACATCCTCTGACAACTCTAGAGATA GAGCGTTCCCCTTCGGGGGACAGAGTGACAGGTGGTG CATGGTTGTCGTCAGCTCGTGTCGTGAGATGTTGGGT TAAGTCCCGCAAC |
| *Paracoccus kondratievae* NC35 (SEQ ID NO: 4) | GCCGCGTGAGTGNNNAAGNCCCTAGGGTTGTAAAGCT CTTTCANCTGGGAAGATAATGACTGTACCAGCAGAAG AAGCCCCGGCTAACTCCGTGCCAGCAGCCGCGGTAAT ACGGAGGGGGCTAGCGTTGTTCGGAATTACTGGGCGT AAAGCGCACGTAGGCGGACCGGAAAGTTGGGGGTGAA ATCCCGGGGCTCAACCCCGGAACTGCCTTCAAAACTA TCGGTCTGGAGTTCGAGAGAGGTGAGTGGAATTCCGA GTGTAGAGGTGAAATTCGTAGATATTCGGAGGAACAC CAGTGGCGAAGGCGGCTCACTGGCTCGATACTGACGC TGAGGTGCGAAAGCGTGGGGAGCAAACAGGATTAGAT ACCCTGGTAGTCCACGCCGTAAACGATGAATGCCAGT CGTCGGGCAGCATGCTGTTCGGTGACACACCTAACGG ATTAAGCATTCCGCCTGGGGAGTACGGTCGCAAGATT AAAACTCAAAGGAATTGACGGGGGCCCGCACAAGCGG |

TABLE 1-continued

| Strain (SEQ ID. NO) | Partial 16S ribosomal RNA sequence |
|---|---|
| | TGGAGCATGTGGTTTAATTCGAAGCAACGCGCAGAAC CTTACCAACCCTTGACATCCCAGGACAGCCCGAGAGA TCGGGTCTCCACTTCGGTGGCCTGGAGACAGGTGCTG CATGGCTGTCGTCAGCTCGTGTCGTGAGATGTTCGGT TAAGTCCGGC |
| Enterobacter cloacae CAP12 (SEQ ID NO: 5) | CTGNNGCAGCCNTGCCGCGTGTATGAAGAAGGNCTTC GGGTTGTAAAGTACTTTCAGCGGGGAGGAAGGTGTTG TGGTTAATAACCACAGCAATTGACGTTACCCGCAGAA GAAGCACCGGCTAACTCCGTGCCAGCAGCCGCGGTAA TACGGAGGGTGCAAGCGTTAATCGGAATTACTGGGCG TAAAGCGCACGCAGGCGGTCTGTCAAGTCGGATGTGA AATCCCCGGGCTCAACCTGGGAACTGCATTCGAAACT GGCAGGCTAGAGTCTTGTAGAGGGGGGTAGAATTCCA GGTGTAGCGGTGAAATGCGTAGAGATCTGGAGGAATA CCGGTGGCGAAGGCGGCCCCCTGGACAAAGACTGACG CTCAGGTGCGAAAGCGTGGGGAGCAAACAGGATTAGA TACCCTGGTAGTCCACGCCGTAAACGATGTCGATTTG GAGGTTGTGCCCTTGAGGCGTGGCTTCCGGAGCTAAC GCGTTAAATCGACCGCCTGGGGAGTACGGCCGCAAGG TTAAAACTCAAATGAATTGACGGGGGCCCGCACAAGC GGTGGAGCATGTGGTTTAATTCGATGCAACGCGAAGA ACCTTACCTGGTCTTGACATCCACAGAACTTTCCAGA GATGGATTGGTGCCTTCGGGAACTGTGAGACAGGTGC TGCATGGCTGTCGTCAGCTCGTGTTGTGAAATGTTGG GTTAAGTCCCGCAACNANNCGCAAC |
| Bacillus nealsonii BOBA57 (SEQ ID NO: 6) | TGNNGGANCAACGCCGCGTGAGTGATGAAGGTTTTCG GATCGTAAAACTCTGTTGTTAGGGAAGAACAAGTACG AGAGTAACTGCTCGTACCTTGACGGTACCTAACCAGA AAGCCACGGCTAACTACGTGCCAGCAGCCGCGGTAAT ACGTAGGTGGCAAGCGTTGTCCGGAATTATTGGGCGT AAAGCGCGCGCAGGCGGTCCTTTAAGTCTGATGTGAA AGCCCACGGCTCAACCGTGGAGGGTCATTGGAAACTG GGGGACTTGAGTGCAGAAGAGAAGAGTGGAATTCCAC GTGTAGCGGTGAAATGCGTAGAGATGTGGAGGAACAC CAGTGGCGAAGGCGACTCTTTGGTCTGTAACTGACGC TGAGGCGCGAAAGCGTGGGGAGCAAACAGGATTAGAT ACCCTGGTAGTCCACGCCGTAAACGATGAGTGCTAAG TGTTAGAGGGTTTCCGCCCTTTAGTGCTGCAGCAAAC GCATTAAGCACTCCGCCTGGGGAGTACGGCCGCAAGG CTGAAACTCAAAGGAATTGACGGGGGCCCGCACAAGC GGTGGAGCATGTGGTTTAATTCGAAGCAACGCGAAGA ACCTTACCAGGTCTTGACATCTCCTGACAATCCTAGA GATAGGACGTTCCCCTTCGGGGACAGGATGACAGGT GGTGCATGGTTGTCGTCAGCTCGTGTCGTGAGATGTT GGGTTAAGTCCCGC |

Methods for determining sequence identity are well known by one of ordinary skill in the art. By way of example and not of limitation, the BLASTn algorithm available through National Center for Biotechnology Information (NCBI) can be used to align sequences and determine their identity.

The foregoing bacterial strains were identified at least to their genus designation by means of conventional biochemistry and morphological indicators. Furthermore, the biochemical assays for confirmed Gram-negative strains such as *Paracoccus kondratievae* and *Enterobacter cloacae* included growth on MacConkey medium and nutrient agar, microscopic examination, growth on 5% and 7.5% NaCl medium, growth at pH 5 and pH 9, growth at 42° C. and 50° C., the ability to produce acid upon fermentation with cellobiose, lactose, glycerol, glucose, sucrose, d-mannitol, and starch; fluorescent pigment production; gelatin hydrolysis; nitrate reduction; starch hydrolysis; oxidase reaction, catalase production, urease production and motility. Similarly, the biochemical assays for confirmed Gram-positive strains such as *Bacillus* included growth on MacConkey medium and nutrient agar, microscopic examination, growth on 5% and 7.5% NaCl medium, growth at pH 5 and pH 9, growth at 42° C. and 50° C., the ability to produce acid upon fermentation with cellobiose, lactose, glycerol, glucose, sucrose, d-mannitol, and starch; fluorescent pigment production; gelatin hydrolysis; nitrate reduction; catalase production, starch hydrolysis; oxidase reaction, urease production and motility.

The present invention also relates to a biologically pure bacterial culture wherein bacteria, i.e. the bacterial strain in the bacterial culture, are mutants of any of the foregoing bacterial strains, which comprises one or more mutations that retain the ability to promote plant growth. Thus, the mutant of any of the foregoing strains will be capable of promoting plant growth when compared to plants to which the mutant was not applied.

The following assays can be used, either individually or in concert, to identify mutant strains, which are capable under gnotobiotic conditions to increase leaf area in 3- to 4-week old whole plants (beaker assay), to increase shoot length or shoot dry weight (soil-plate assay), or to increase root length, root dry weight, shoot dry weight and shoot length (growth pouch assay), which are positively correlated with the ability to promote growth directly in whole plants grown in raw (nonsterilized) soil. In a "Beaker Assay," a mixture of field soil and perlite is sterilized, e.g., by gamma-irradiation (about 1 mRad has proved suitable). Samples of the mix are transferred aseptically to sterile, covered beakers, to which enough water or nutrient solution is added to achieve a moisture content of roughly 25%. Surface-sterilized seed of a test plant, such as rape (*Brassica napus* and *Brassica campestris*), radish, wheat, soybean, corn or cotton, are then sown (1 seed per beaker) after briefly incubating in an aqueous bacterial cell suspension of the strain under study. (A bacterial concentration in the range of $10^9$ colony forming units (CFU) per ml of suspension has proved suitable for this purpose.) After seedlings have developed, under controlled conditions suitable to the test plant, to a point where mature leaves have grown, those plants subjected to bacterial treatments are compared against uninoculated controls to ascertain differences in leaf area between test and control groups.

In a "Soil-plate Assay," Petri plates are filled with ground, air-dried soil that has been sterilized by autoclaving, gamma-irradiation, etc. The soil in each plate is then moistened and left covered overnight to assure a uniform moisture distribution through the soil. Inoculated (test) and control seeds, as described above, are thereafter sown in each plate, some six to eight seeds per plate at about 1 cm depth, and grown in the dark under appropriate conditions of temperature and humidity until shoots develop. At the end of incubation, the shoot lengths are determined. In a "Growth Pouch Assay," cellophane containers of the type heretofore used as seed-pack growth pouches are filled with a small volume of deionized water or mineral solution and autoclaved to assure sterility. Test seeds incubated in a bacterial suspension, as previously described, and control seeds not exposed to the bacteria are aseptically sown, about six seeds to a pouch, respectively, and are germinated in the dark under suitable, controlled conditions. After shoots have developed, the pouches are opened and the seedling root length, root dry weight, shoot length and shoot dry weight determined for both tests and controls. Alternatively, the mutant strains can be tested as shown in the Examples for any of the foregoing bacterial strains with respect to the ability to promote plant growth.

The present invention is also directed to an inoculum for application to plants, plant seeds, or a plant growth medium, wherein the inoculum comprises an effective amount of a biologically pure bacterial culture of *Bacillus aryabhattai* strain CAP53 (NRRL No. B-50819), *Bacillus aryabhattai* strain CAP56 (NRRL No. B-50817), *Bacillus flexus* strain BT054 (NRRL No. B-50816v), *Paracoccus kondratievae* strain NC35 (NRRL No. B-50820), *Enterobacter cloacae* strain CAP12 (NRRL No. B-50822), *Bacillus nealsonii* strain BOBA57 (NRRL No. B-50821), or a mutant of any of the foregoing strains, and an agriculturally acceptable carrier.

Alternatively, the inoculum of the present invention can include an effective amount of a mixture comprising at least two biologically pure bacterial cultures described herein. Thus, the mixture of two biologically pure bacterial cultures can include *Bacillus aryabhattai* strain CAP53 and *Bacillus aryabhattai* strain CAP56; *Bacillus aryabhattai* strain CAP53 and *Bacillus flexus* strain BT054; *Bacillus aryabhattai* strain CAP53 and *Paracoccus kondratievae* strain NC35; *Bacillus aryabhattai* strain CAP53 and *Enterobacter cloacae* strain CAP12; *Bacillus aryabhattai* strain CAP53 and *Bacillus nealsonii* strain BOBA57; *Bacillus aryabhattai* strain CAP56 and *Bacillus flexus* strain BT054; *Bacillus aryabhattai* strain CAP56 and *Paracoccus kondratievae* strain NC35; *Bacillus aryabhattai* strain CAP56 and *Enterobacter cloacae* strain CAP12; *Bacillus aryabhattai* strain CAP56 and *Bacillus nealsonii* strain BOBA57; *Bacillus flexus* strain BT054 and *Paracoccus kondratievae* strain NC35; *Bacillus flexus* strain BT054 and *Enterobacter cloacae* strain CAP12; *Bacillus flexus* strain BT054 and *Bacillus nealsonii* strain BOBA57; *Paracoccus kondratievae* strain NC35 and *Enterobacter cloacae* strain CAP12; *Paracoccus kondratievae* strain NC35 and *Bacillus nealsonii* strain BOBA57; or *Enterobacter cloacae* strain CAP12 and *Bacillus nealsonii* strain BOBA57.

An inoculum which includes an effective amount of a mixture of three bacteriologically pure bacterial cultures can include *Bacillus aryabhattai* strain CAP53, *Bacillus aryabhattai* strain CAP56, and *Bacillus flexus* strain BT054; *Bacillus aryabhattai* strain CAP53, *Bacillus aryabhattai* strain CAP56, and *Paracoccus kondratievae* strain NC35; *Bacillus aryabhattai* strain CAP53, *Bacillus aryabhattai* strain CAP56, and *Enterobacter cloacae* strain CAP12; *Bacillus aryabhattai* strain CAP53, *Bacillus aryabhattai* strain CAP56, and *Bacillus nealsonii* strain BOBA57; *Bacillus aryabhattai* strain CAP53, *Bacillus flexus* strain BT054, and *Paracoccus kondratievae* strain NC35; *Bacillus aryabhattai* strain CAP53, *Bacillus flexus* strain BT054, and *Enterobacter cloacae* strain CAP12; *Bacillus aryabhattai* strain CAP53, *Bacillus flexus* strain BT054, and *Bacillus nealsonii* strain BOBA57; *Bacillus aryabhattai* strain CAP53, *Paracoccus kondratievae* strain NC35, and *Enterobacter cloacae* strain CAP12; *Bacillus aryabhattai* strain CAP53, *Paracoccus kondratievae* strain NC35, and *Bacillus nealsonii* strain BOBA57; *Bacillus aryabhattai* strain CAP56, *Bacillus flexus* strain BT054, and *Paracoccus kondratievae* strain NC35; *Bacillus aryabhattai* strain CAP56, *Bacillus flexus* strain BT054, and *Enterobacter cloacae* strain CAP12; *Bacillus aryabhattai* strain CAP56, *Bacillus flexus* strain BT054, and *Bacillus nealsonii* strain BOBA57; *Bacillus aryabhattai* strain CAP56, *Paracoccus kondratievae* strain NC35, and *Enterobacter cloacae* strain CAP12; *Bacillus aryabhattai* strain CAP56, *Paracoccus kondratievae* strain NC35, and *Bacillus nealsonii* strain BOBA57; *Bacillus aryabhattai* strain CAP56, *Enterobacter cloacae* strain CAP12, and *Bacillus nealsonii* strain BOBA57; *Bacillus flexus* strain BT054, *Paracoccus kondratievae* strain NC35, and *Enterobacter cloacae* strain CAP12; *Bacillus flexus* strain BT054, *Paracoccus kondratievae* strain NC35, and *Bacillus nealsonii* strain BOBA57; *Bacillus flexus* strair BT054, *Enterobacter cloacae* strain CAP12, and *Bacillus nealsonii* strain BOBA57; or *Paracoccus kondratievae* strain NC35, *Enterobacter cloacae* strain CAP12, and *Bacillus nealsonii* strain BOBA57.

The following mixtures of bacteriologically pure bacterial cultures are favorable for use in stimulating plant growth. They include, without limitation, mixtures of: (1) *Enterobacter cloacae* CAP12 and *Bacillus aryabhattai* CAP53; (2) *Enterobacter cloacae* CAP12 and *Bacillus aryabhattai* CAP56; (3) *Enterobacter cloacae* CAP12 and *Bacillus flexus* BT054; (4) *Enterobacter cloacae* CAP12 and *Bacillus nealsonii* BOBA57; (5) *Bacillus aryabhattai* CAP53 and *Bacillus aryabhattai* CAP56; and (6) *Bacillus flexus* BT054 and *Bacillus aryabhattai* CAP56.

Rhizobacteria are root-colonizing bacteria that form symbiotic relationships with many plants, and as such are useful in promoting plant growth. Accordingly, any of the inoculums of the present invention regardless of whether they contains a single bacterial strain disclosed herein or a mixture of two or more such bacterial strains can also include an effective amount of rhizobacteria.

Such rhizobacteria can be present as a biologically pure bacterial culture. Alternatively, rhizobacteria that are used in the inoculums of the present invention can include two or more strains of rhizobacteria. By way of example and not of limitation, the rhizobacteria can include *Bradyrhizobium* genus bacteria, *Rhizobium* genus bacteria, or a combination thereof. Also, the *Bradirhizobium* genus bacteria can comprise *Bradyrhizobium japonicum*, and the *Rhizobium* genus bacteria can comprise *Rhizobium phaseoli*, *Rhizobium leguminosarum*, or a combination thereof. The inclusion of rhizobacteria in the present compositions and methods is especially advantageous in so-called "virgin soils" which do not contain an indigenous population of PGPB such as nitrogen fixing rhizobia. This may occur e.g. where nitrogen-fixing legume crops have not been previously or recently grown.

In addition to one or more biologically pure bacterial cultures as described in the foregoing sections, an inoculum of the present invention also comprises an agriculturally acceptable carrier. The carrier can include a dispersant, a surfactant, an additive, water, a thickener, an anti-caking agent, residue breakdown, a composting formulation, a granular application, diatomaceous earth, an oil, a coloring agent, a stabilizer, a preservative, a polymer, a coating, or a combination thereof. One of ordinary skill in the art can readily determine the appropriate carrier to be used taking into consideration factors such as a particular bacterial strain, plant to which the inoculum is to be applied, type of soil, climate conditions, whether the inoculum is in liquid, solid or powder form, and the like.

The additive can comprise an oil, a gum, a resin, a clay, a polyoxyethylene glycol, a terpene, a viscid organic, a fatty acid ester, a sulfated alcohol, an alkyl sulfonate, a petroleum sulfonate, an alcohol sulfate, a sodium alkyl butane diamate, a polyester of sodium thiobutant dioate, a benzene acetonitrile derivative, a proteinaceous material, or a combination thereof.

The proteinaceous material can include a milk product, wheat flour, soybean meal, blood, albumin, gelatin, or a combination thereof.

The thickener can comprise a long chain alkylsulfonate of polyethylene glycol, polyoxyethylene oleate, or a combination thereof.

The surfactant can contain a heavy petroleum oil, a heavy petroleum distillate, a polyol fatty acid ester, a polyethoxylated fatty acid ester, an aryl alkyl polyoxyethylene glycol, an alkyl amine acetate, an alkyl aryl sulfonate, a polyhydric alcohol, an alkyl phosphate, or a combination thereof.

The anti-caking agent can include a sodium salt such as a sodium sulfite, a sodium sulfate, a sodium salt of monomethyl naphthalene sulfonate, a sodium salt of dimethyl naphthalene sulfonate, or a combination thereof; or a calcium salt such as calcium carbonate, diatomaceous earth, or a combination thereof.

Any agriculturally acceptable carrier can be used. Such carriers include, but are not limited to, vermiculite, charcoal, sugar factory carbonation press mud, rice husk, carboxymethyl cellulose, peat, perlite, fine sand, calcium carbonate, flour, alum, a starch, talc, polyvinyl pyrrolidone, or a combination thereof.

Inoculants can be prepared as solid, liquid or powdered formulations as is known in the art. The inoculum of the present invention can be formulated as a seed coating formulation, a liquid formulation for application to plants or to a plant growth medium, or a solid formulation for application to plants or to a plant growth medium.

When the inoculum is prepared as a liquid formulation for application to plants or to a plant growth medium, it can be prepared in a concentrated formulation or a working form formulation. In some instances, the seed coating formulation of the present invention is an aqueous or oil-based solution for application to seeds.

When the inoculum of the present invention is prepared as a solid formulation for application to plants or to a plant growth medium, it can be prepared as a granular formulation or a powder agent. The seed coating formulation can be a powder or granular formulation for application to seeds.

The inoculum can further include an agrochemical such as a fertilizer, a micronutrient fertilizer material, an insecticide, a herbicide, a plant growth amendment, a fungicide, a molluscicide, an algicide, a bacterial inoculant, a fungal inoculant, or a combination thereof. In some instances, the fertilizer is a liquid fertilizer. The agrochemical can either be applied to a plant growth medium or to plants and/or seeds. Liquid fertilizer can include, without limitation, ammonium sulfate, ammonium nitrate, ammonium sulfate nitrate, ammonium chloride, ammonium bisulfate, ammonium polysulfide, ammonium thiosulfate, aqueous ammonia, anhydrous ammonia, ammonium polyphosphate, aluminum sulfate, calcium nitrate, calcium ammonium nitrate, calcium sulfate, calcined magnesite, calcitic limestone, calcium oxide, calcium nitrate, dolomitic limestone, hydrated lime, calcium carbonate, diammonium phosphate, monoammonium phosphate, magnesium nitrate, magnesium sulfate, potassium nitrate, potassium chloride, potassium magnesium sulfate, potassium sulfate, sodium nitrates, magnesian limestone, magnesia, urea, urea-formaldehydes, urea ammonium nitrate, sulfur-coated urea, polymer-coated urea, isobutylidene diurea, $K_2SO_4$-$2MgSO_4$, kainite, sylvinite, kieserite, Epsom salts, elemental sulfur, marl, ground oyster shells, fish meal, oil cakes, fish manure, blood meal, rock phosphate, super phosphates, slag, bone meal, wood ash, manure, bat guano, peat moss, compost, green sand, cottonseed meal, feather meal, crab meal, fish emulsion, or a combination thereof.

The micronutrient fertilizer material can comprise boric acid, a borate, a boron frit, copper sulfate, a copper frit, a copper chelate, a sodium tetraborate decahydrate, an iron sulfate, an iron oxide, iron ammonium sulfate, an iron frit, an iron chelate, a manganese sulfate, a manganese oxide, a manganese chelate, a manganese chloride, a manganese frit, a sodium molybdate, molybdic acid, a zinc sulfate, a zinc oxide, a zinc carbonate, a zinc frit, zinc phosphate, a zinc chelate, or a combination thereof.

The insecticide can include an organophosphate, a carbamate, a pyrethroid, an acaricide, an alkyl phthalate, boric acid, a borate, a fluoride, sulfur, a haloaromatic substituted urea, a hydrocarbon ester, a biologically-based insecticide, or a combination thereof.

The herbicide can comprise a chlorophenoxy compound, a nitrophenolic compound, a nitrocresolic compound, a dipyridyl compound, an acetamide, an aliphatic acid, an anilide, a benzamide, a benzoic acid, a benzoic acid derivative, anisic acid, an anisic acid derivative, a benzonitrile, benzothiadiazinone dioxide, a thiocarbamate, a carbamate, a carbanilate, chloropyridinyl, a cyclohexenone derivative, a dinitroaminobenzene derivative, a fluorodinitrotoluidine compound, isoxazolidinone, nicotinic acid, isopropylamine, an isopropylamine derivative, oxadiazolinone, a phosphate, a phthalate, a picolinic acid compound, a triazine, a triazole, a uracil, a urea derivative, endothall, sodium chlorate, or a combination thereof.

The fungicide can comprise a substituted benzene, a thiocarbamate, an ethylene bis dithiocarbamate, a thiophthalidamide, a copper compound, an organomercury compound, an organotin compound, a cadmium compound, anilazine, benomyl, cyclohexamide, dodine, etridiazole, iprodione, metlaxyl, thiamimefon, triforine, or a combination thereof.

The fungal inoculant can comprise a fungal inoculant of the family Glomeraceae, a fungal inoculant of the family Claroidoglomeraceae, a fungal inoculant of the family Gigasporaceae, a fungal inoculant of the family Acaulosporaceae, a fungal inoculant of the family Sacculosporaceae, a fungal inoculant of the family Entrophosporaceae, a fungal inoculant of the family Pacidsporaceae, a fungal inoculant of the family Diversisporaceae, a fungal inoculant of the family Paraglomeraceae, a fungal inoculant of the family Archaeosporaceae, a fungal inoculant of the family Geosiphonaceae, a fungal inoculant of the family Ambisporaceae, a fungal inoculant of the family Scutellosporaceae, a fungal inoculant of the family Dentiscultataceae, a fungal inoculant of the family Racocetraceae, a fungal inoculant of the phylum Basidiomycota, a fungal inoculant of the phylum Ascomycota, a fungal inoculant of the phylum Zygomycota, or a combination thereof.

The bacterial inoculant, for purposes of the present invention, can include a bacterial inoculant of the genus *Rhizobium*, a bacterial inoculant of the genus *Bradyrhizobium*, a bacterial inoculant of the genus *Mesorhizobium*, a bacterial inoculant of the genus *Azorhizobium*, a bacterial inoculant of the genus *Allorhizobium*, a bacterial inoculant of the genus *Sinorhizobium*, a bacterial inoculant of the genus *Kluyvera*, a bacterial inoculant of the genus *Azotobacter*, a bacterial inoculant of the genus *Pseudomonas*, a bacterial inoculant of the genus *Azospirillium*, a bacterial inoculant of the genus *Bacillus*, a bacterial inoculant of the genus *Streptomyces*, a bacterial inoculant of the genus *Paenibacillus*, a bacterial inoculant of the genus *Paracoccus*, a bacterial inoculant of the genus *Enterobacter*, a bacterial inoculant of the genus *Alcaligenes*, a bacterial inoculant of the genus *Mycobacterium*, a bacterial inoculant of the genus *Trichoderma*, a bacterial inoculant of the genus *Gliocladium*, a bacterial inoculant of the genus *Glomus*, a bacterial inoculant of the genus *Klebsiella*, or a combination thereof.

All of the biologically pure bacterial cultures and inoculums of the present invention can be used in methods for stimulating plant growth. Such methods include applying the foregoing cultures and inoculums to a plant, plant seed, or plant growth medium in order to stimulate growth of the plant. Techniques for applying inoculants to plants are known in the art, including appropriate modes of administration, frequency of administration, dosages, and the like. The inoculant can be applied to the soil prior to, contemporaneously with, or after sowing seeds, after planting, or after plants have emerged from the ground. The inoculant can also be applied to seeds themselves prior to or at the time of planting (e.g., packaged seed may be sold with the inoculant already applied). The inoculant can also be applied to the plant after it has emerged from the ground, or to the leaves, stems, roots, or other parts of the plant.

The method for stimulating plant growth can include applying a substance such as glycerol, pyruvate, yeast extract, or polyol to the plant growth medium. Any of the polyols (sugar alcohols) can be used, with the preferred one being mannitol. For the preparation of yeast extract, *Saccharomyces cerevisiae* is a preferred yeast starting material, although several other yeast strains may be useful to produce yeast ferment materials used in the compositions and methods described herein. Additional yeast strains that can be used instead of or in addition to *Saccharomyces cerevisiae* include *Kluyveromyces marxianus, Kluyveromyces lactis, Candida utilis* (Torula yeast), *Zygosaccharomyces, Pichia pastoris*, and *Hansanula polymorpha*, and others known to those skilled in the art.

In instances in which the substance is applied to a plant growth medium, at least one bacterial culture or at least one inoculum of the present invention can be applied to a plant or plant seed in the plant growth medium, or to the plant growth medium. Preferably, the inoculum is applied to the plant growth medium as a solid or liquid formulation. The bacterial culture or inoculum and the chemical can be applied contemporaneously or at separate times. The exact order is not of great relevance, and the optimal combination can be determined empirically by one of ordinary skill in the art without due experimentation. For example, a skilled artisan can set up experimental conditions wherein: (1) the inoculum or bacterial culture and the substance are administered concurrently, (2) the inoculum or bacterial culture is administered on a separate occasion after the substance is added to a plant growth medium, (3) the inoculum or bacterial culture is administered on a separate occasion prior to the substance being added to a plant growth medium, and the like. The results of such and similar experimental designs can easily demonstrate the most suitable methods for application of the bacterial strain or inoculum and the substance. Thus, the bacterial culture or inoculum of the present invention can be applied to a plant growth medium prior to, concurrently with, or after planting of seeds, seedlings, cuttings, bulbs, or plants in the plant growth medium.

The plant growth medium includes soil, water, an aqueous solution, sand, gravel, a polysaccharide, mulch, compost, peat moss, straw, logs, clay, or a combination thereof. Preferably, the plant growth medium is soil or compost. As is known in the art, the plant growth medium can be stored for future planting.

For purposes of the compositions and methods of the present invention, the plant can be a dicotyledon, a monocotyledon or a gymnosperm.

The dicotyledon can be selected from the group consisting of bean, pea, tomato, pepper, squash, alfalfa, almond, aniseseed, apple, apricot, arracha, artichoke, avocado, bambara groundnut, beet, bergamot, black pepper, black wattle, blackberry, blueberry, bitter orange, bok-choi, Brazil nut, breadfruit, broccoli, broad bean, Brussels sprouts, buckwheat, cabbage, camelina, Chinese cabbage, cacao, cantaloupe, caraway seeds, cardoon, carob, carrot, cashew nuts, cassava, castor bean, cauliflower, celeriac, celery, cherry, chestnut, chickpea, chicory, chili pepper, chrysanthemum, cinnamon, citron, clementine, clove, clover, coffee, cola nut, colza, corn, cotton, cottonseed, cowpea, crambe, cranberry, cress, cucumber, currant, custard apple, drumstick tree, earth pea, eggplant, endive, fennel, fenugreek, fig, filbert, flax, geranium, gooseberry, gourd, grape, grapefruit, guava, hemp, hempseed, henna, hop, horse bean, horseradish, indigo, jasmine, Jerusalem artichoke, jute, kale, kapok, kenaf, kohlrabi, kumquat, lavender, lemon, lentil, lespedeza, lettuce, lime, liquorice, litchi, loquat, lupine, macadamia nut, mace, mandarin, mangel, mango, medlar, melon, mint, mulberry, mustard, nectarine, niger seed, nutmeg, okra, olive, opium, orange, papaya, parsnip, pea, peach, peanut, pear, pecan nut, persimmon, pigeon pea, pistachio nut, plantain, plum, pomegranate, pomelo, poppy seed, potato, sweet potato, prune, pumpkin, quebracho, quince, trees of the genus *Cinchona*, quinoa, radish, ramie, rapeseed, raspberry, rhea, rhubarb, rose, rubber, rutabaga, safflower, sainfoin, salsify, sapodilla, Satsuma, scorzonera, sesame, shea tree, soybean, spinach, squash, strawberry, sugar beet, sugarcane, sunflower, swede, sweet pepper, tangerine, tea, teff, tobacco, tomato, trefoil, tung tree, turnip, arena, vetch, walnut, watermelon, yerba mate, wintercress, shepherd's purse, garden cress, peppercress, watercress, pennycress, star anise, laurel, bay laurel, cassia, jamun, dill, tamarind, peppermint, oregano, rosemary, sage, soursop, pennywort, calophyllum, balsam pear, kukui nut, Tahitian chestnut, basil, huckleberry, hibiscus, passionfruit, star apple, sassafras, cactus, St. John's wort, loosestrife, hawthorn, cilantro, curry plant, kiwi, thyme, zucchini, ulluco, jicama, waterleaf, spiny monkey orange, yellow mombin, starfruit, amaranth, wasabi, Japanese pepper, yellow plum, mashua, Chinese toon, New Zealand spinach, bower spinach, ugu, tansy, chickweed, jocote, Malay apple, paracress, sowthistle, Chinese potato, horse parsley, hedge mustard, campion, agate, cassod tree, thistle, burnet, star gooseberry, saltwort, glasswort, sorrel, silver lace fern, collard greens, primrose, cowslip, purslane, knotgrass, terebinth, tree lettuce, wild betel, West African pepper, yerba santa, tarragon, parsley, chervil, land cress, burnet saxifrage, honeyherb, butterbur, shiso, water pepper, perilla, bitter bean, oca, kampong, Chinese celery, lemon basil, Thai basil, water mimosa, cicely, cabbage-tree, moringa, mauka, ostrich fern, rice paddy herb, yellow sawah lettuce, lovage, pepper grass, maca, bottle gourd, hyacinth bean, water spinach, catsear, fishwort, Okinawan spinach, lotus sweetjuice, gallant soldier, culantro, arugula, cardoon, caigua, mitsuba, chipilin, samphire, mampat, ebolo, ivy gourd, cabbage thistle, sea kale, chaya, huauzontle, Ethiopian mustard, magenta spreen, good king henry, epazole, lamb's quarters, centella plumed cockscomb, caper, rapini, napa cabbage, mizuna, Chinese savoy, kai-lan, mustard greens, Malabar spinach, chard, marshmallow, climbing wattle, China jute, paprika, annatto seed, spearmint, savory, marjoram, cumin, chamomile, lemon balm, allspice, bilberry, cherimoya, cloudberry, damson, pitaya, durian, elderberry, feijoa, jackfruit, jambul, jujube, physalis, purple mangosteen, rambutan, redcurrant, blackcurrant, salal berry, satsuma, ugli fruit, azuki bean, black bean, black-eyed pea, borlotti bean, common bean, green bean, kidney bean, lima bean, mung bean, navy bean, pinto bean, runner bean, mangetout, snap pea, broccoflower, calabrese, nettle, bell pepper, raddichio, daikon, white radish, skirret, tat soi, broccolini, black radish, burdock root, fava bean, broccoli raab, lablab, lupin, sterculia, velvet beans, winged beans, yam beans, mulga, ironweed, umbrella bush, tjuntjula, wakalpulka, witchetty bush, wiry wattle, chia, beech nut, candlenut, colocynth, mamoncillo, Maya nut, mongongo, ogbono nut, paradise nut, and cempedak.

The dicotyledon can be from a family selected from the group consisting of Acanthaceae (acanthus), Aceraceae (maple), Achariaceae, Achatocarpaceae (achatocarpus), Actinidiaceae (Chinese gooseberry), Adoxaceae (moschatel), Aextoxicaceae, Aizoaceae (fig marigold), Akaniaceae, Alangiaceae, Alseuosmiaceae, Alzateaceae, Amaranthaceae (amaranth), Amborellaceae, Anacardiaceae (sumac), Ancistrocladaceae, Anisophylleaceae, Annonaceae (custard apple), Apiaceae (carrot), Apocynaceae (dogbane), Aquifoliaceae (holly), Araliaceae (ginseng), Aristolochiaceae (birthwort), Asclepiadaceae (milkweed), Asteraceae (aster), Austrobaileyaceae, Balanopaceae, Balanophoraceae (balanophora), Balsaminaceae (touch-me-not), Barbeyaceae, Barclayaceae, Basellaceae (basella), Bataceae (saltwort), Begoniaceae (begonia), Berberidaceae (barberry), Betulaceae (birch), Bignoniaceae (trumpet creeper), Bixaceae (lipstick tree), Bombacaceae (kapok tree), Boraginaceae (borage), Brassicaceae (mustard, also Cruciferae), Bretschneideraceae, Brunelliaceae (brunellia), Bruniaceae, Brunoniaceae, Buddlejaceae (butterfly bush), Burseraceae (frankincense), Buxaceae (boxwood), Byblidaceae, Cabombaceae (water shield), Cactaceae (cactus), Caesalpiniaceae, Callitrichaceae (water starwort), Calycanthaceae (strawberry shrub), Calyceraceae (calycera), Campanulaceae (bellflower), Canellaceae (canella), Cannabaceae (hemp), Capparaceae (caper), Caprifoliaceae (honeysuckle), Cardiopteridaceae, Caricaceae (papaya), Caryocaraceae (souari), Caryophyllaceae (pink), Casuarinaceae (she-oak), Cecropiaceae (cecropia), Celastraceae (bittersweet), Cephalotaceae, Ceratophyllaceae (hornwort), Cercidiphyllaceae (katsura tree), Chenopodiaceae (goosefoot), Chloranthaceae (chloranthus), Chrysobalanaceae (cocoa plum), Circaeasteraceae, Cistaceae (rockrose), Clethraceae (clethra), Clusiaceae (mangosteen, also Guttiferae), Cneoraceae, Columelliaceae, Combretaceae (Indian almond), Compositae (aster), Connaraceae (cannarus), Convolvulaceae (morning glory), Coriariaceae, Cornaceae (dogwood), Corynocarpaceae (karaka), Crassulaceae (stonecrop), Crossosomataceae (crossosoma), Crypteroniaceae, Cucurbitaceae (cucumber), Cunoniaceae (cunonia), Cuscutaceae (dodder), Cyrillaceae (cyrilla), Daphniphyllaceae, Datiscaceae (datisca), Davidsoniaceae, Degeneriaceae, Dialypetalanthaceae, Diapensiaceae (diapensia), Dichapetalaceae, Didiereaceae, Didymelaceae, Dilleniaceae (dillenia), Dioncophyllaceae, Dipentodontaceae, Dipsacaceae (teasel), Dipterocarpaceae (meranti), Donatiaceae, Droseraceae (sundew), Duckeodendraceae, Ebenaceae (ebony), Elaeagnaceae (oleaster), Elaeocarpaceae (elaeocarpus), Elatinaceae (waterwort), Empetraceae (crowberry), Epacridaceae (epacris), Eremolepidaceae (catkin-mistletoe), Ericaceae (heath), Erythroxylaceae (coca), Eucommiaceae, Eucryphiaceae, Euphorbiaceae (spurge), Eupomatiaceae, Eupteleaceae, Fabaceae (pea or legume), Fagaceae (beech), Flacourtiaceae (flacourtia), Fouquieriaceae (ocotillo), Frankeniaceae (frankenia), Fumariaceae (fumitory), Garryaceae (silk tassel), Geissolomataceae, Gentianaceae (gentian), Geraniaceae (geranium), Gesneriaceae (gesneriad), Globulariaceae, Gomortegaceae, Goodeniaceae (goodenia), Greyiaceae, Grossulariaceae (currant), Grubbiaceae, Gunneraceae (gunnera), Gyrostemonaceae, Haloragaceae (water milfoil), Hamamelidaceae (witch hazel), Hernandiaceae (hernandia), Himantandraceae, Hippocastanaceae (horse chestnut), Hippocrateaceae (hippocratea), Hippuridaceae (mare's tail), Hoplestigmataceae, Huaceae, Hugoniaceae, Humiriaceae, Hydnoraceae, Hydrangeaceae (hydrangea), Hydrophyllaceae (waterleaf), Hydrostachyaceae, Icacinaceae (icacina), Idiospermaceae, Illiciaceae (star anise), Ixonanthaceae, Juglandaceae (walnut), Julianiaceae, Krameriaceae (krameria), Lacistemataceae, Lamiaceae (mint, also Labiatae), Lardizabalaceae (lardizabala), Lauraceae (laurel), Lecythidaceae (brazil nut), Leeaceae, Leitneriaceae (corkwood), Lennoaceae (lennoa), Lentibulariaceae (bladderwort), Limnanthaceae (meadow foam), Linaceae (flax), Lissocarpaceae, Loasaceae (loasa), Loganiaceae (logania), Loranthaceae (showy mistletoe), Lythraceae (loosestrife), Magnoliaceae (magnolia), Malesherbiaceae, Malpighiaceae (barbados cherry), Malvaceae (mallow), Marcgraviaceae (shingle plant), Medusagynaceae, Medusandraceae, Melastomataceae (melastome), Meliaceae (mahogany), Melianthaceae, Mendonciaceae, Menispermaceae (moonseed), Menyanthaceae (buckbean), Mimosaceae, Misodendraceae, Mitrastemonaceae, Molluginaceae (carpetweed), Monimiaceae (monimia), Monotropaceae (Indian pipe), Moraceae (mulberry), Moringaceae (horseradish tree), Myoporaceae (myoporum), Myricaceae (bayberry), Myristicaceae (nutmeg), Myrothamnaceae, Myrsinaceae (myrsine), Myrtaceae (myrtle), Nelumbonaceae (lotus lily), Nepenthaceae (East Indian pitcherplant), Neuradaceae, Nolanaceae, Nothofagaceae, Nyctaginaceae (four-o'clock), Nymphaeaceae (water lily), Nyssaceae (sour gum), Ochnaceae (ochna), Olacaceae (olax), Oleaceae (olive), Oliniaceae, Onagraceae (evening primrose), Oncothecaceae, Opiliaceae, Orobanchaceae (broom rape), Oxalidaceae (wood sorrel), Paeoniaceae (peony), Pandaceae, Papaveraceae (poppy), Papilionaceae, Paracryphiaceae, Passifloraceae (passionflower), Pedaliaceae (sesame), Pellicieraceae, Penaeaceae, Pentaphragmataceae, Pentaphylacaceae, Peridiscaceae, Physenaceae, Phytolaccaceae (pokeweed), Piperaceae (pepper), Pittosporaceae (pittosporum), Plantaginaceae (plantain), Platanaceae (plane tree), Plumbaginaceae (leadwort), Podostemaceae (river weed), Polemoniaceae (phlox), Polygalaceae (milkwort), Polygonaceae (buckwheat), Portulacaceae (purslane), Primulaceae (primrose), Proteaceae (protea), Punicaceae (pomegranate), Pyrolaceae (shinleaf), Quiinaceae, Rafflesiaceae (rafflesia), Ranunculaceae (buttercup orranunculus), Resedaceae (mignonette), Retziaceae, Rhabdodendraceae, Rhamnaceae (buckthorn), Rhizophoraceae (red mangrove), Rhoipteleaceae, Rhynchocalycaceae, Rosaceae (rose), Rubiaceae (madder), Rutaceae (rue), Sabiaceae (sabia), Saccifoliaceae, Salicaceae (willow), Salvadoraceae, Santalaceae (sandalwood), Sapindaceae (soapberry), Sapotaceae (sapodilla), Sarcolaenaceae, Sargentodoxaceae, Sarraceniaceae (pitcher plant), Saururaceae (lizard's tail), Saxifragaceae (saxifrage), Schisandraceae (schisandra), Scrophulariaceae (figwort), Scyphostegiaceae, Scytopetalaceae, Simaroubaceae (quassia), Simmondsiaceae (jojoba), Solanaceae (potato), Sonneratiaceae (sonneratia), Sphaerosepalaceae, Sphenocleaceae (spenoclea), Stackhousiaceae (stackhousia), Stachyuraceae, Staphyleaceae (bladdernut), Sterculiaceae (cacao), Stylidiaceae, Styracaceae (storax), Surianaceae (suriana), Symplocaceae (sweetleaf), Tamaricaceae (tamarix), Tepuianthaceae, Tetracentraceae, Tetrameristaceae, Theaceae (tea), Theligonaceae, Theophrastaceae (theophrasta), Thymelaeaceae (mezereum), Ticodendraceae, Tiliaceae (linden), Tovariaceae, Trapaceae (water chestnut), Tremandraceae, Trigoniaceae, Trimeniaceae, Trochodendraceae, Tropaeolaceae (nasturtium), Turneraceae (turnera), Ulmaceae (elm), Urticaceae (nettle), Valerianaceae (valerian), Verbenaceae (verbena), Violaceae (violet), Viscaceae (Christmas mistletoe), Vitaceae (grape), Vochysiaceae, Winteraceae (wintera), Xanthophyllaceae, and Zygophyllaceae (creosote bush).

The monocotyledon can be selected from the group consisting of corn, wheat, oat, rice, barley, millet, banana, onion, garlic, asparagus, ryegrass, millet, fonio, raishan, nipa grass, turmeric, saffron, galangal, chive, cardamom, date palm, pineapple, shallot, leek, scallion, water chestnut, ramp, Job's tears, bamboo, ragi, spotless watermeal, arrowleaf elephant ear, Tahitian spinach, abaca, areca, bajra, betel nut, broom millet, broom sorghum, citronella, coconut, cocoyam, maize, dasheen, durra, durum wheat, edo, fique, formio, ginger, orchard grass, esparto grass, Sudan grass, guinea corn, Manila hemp, henequen, hybrid maize, jowar, lemon grass, maguey, bulrush millet, finger millet, foxtail millet, Japanese millet, proso millet, New Zealand flax, oats, oil palm, palm palmyra, sago palm, redtop, sisal, sorghum, spelt wheat, sweet corn, sweet sorghum, taro, teff, timothy grass, triticale, vanilla, wheat, and yam.

Alternatively, the monocotyledon can be selected from a family selected from the group consisting of Acoraceae (calamus), Agavaceae (century plant), Alismataceae (water plantain), Aloeaceae (aloe), Aponogetonaceae (cape pondweed), Araceae (arum), Arecaceae (palm), Bromeliaceae (bromeliad), Burmanniaceae (burmannia), Butomaceae (flowering rush), Cannaceae (canna), Centrolepidaceae, Commelinaceae (spiderwort), Corsiaceae, Costaceae (costus), Cyanastraceae, Cyclanthaceae (Panama hat), Cymodoceaceae (manatee grass), Cyperaceae (sedge), Dioscoreaceae (yam), Eriocaulaceae (pipewort), Flagellariaceae, Geosiridaceae, Haemodoraceae (bloodwort), Hanguanaceae (hanguana), Heliconiaceae (heliconia), Hydatellaceae, Hydrocharitaceae (tape grass), Iridaceae (iris), Joinvilleaceae (joinvillea), Juncaceae (rush), Juncaginaceae (arrow grass), Lemnaceae (duckweed), Liliaceae (lily), Limnocharitaceae (water poppy), Lowiaceae, Marantaceae (prayer plant), Mayacaceae (mayaca), Musaceae (banana), Najadaceae (water nymph), Orchidaceae (orchid), Pandanaceae (screw pine), Petrosaviaceae, Philydraceae (philydraceae), Poaceae (grass), Pontederiaceae (water hyacinth), Posidoniaceae (posidonia), Potamogetonaceae (pondweed), Rapateaceae, Restionaceae, Ruppiaceae (ditch grass), Scheuchzeriaceae (scheuchzeria), Smilacaceae (catbrier), Sparganiaceae (bur reed), Stemonaceae (stemona), Strelitziaceae, Taccaceae (tacca), Thurniaceae, Triuridaceae, Typhaceae (cattail), Velloziaceae, Xanthorrhoeaceae, Xyridaceae (yellow-eyed grass), Zannichelliaceae (horned pondweed), Zingiberaceae (ginger), and Zosteraceae (eelgrass).

The gymnosperm can be selected from a family selected from the group consisting of Araucariaceae, Boweniaceae, Cephalotaxaceae, Cupressaceae, Cycadaceae, Ephedraceae, Ginkgoaceae, Gnetaceae, Pinaceae, Podocarpaceae, Taxaceae, Taxodiaceae, Welwitschiaceae, and Zamiaceae.

The stimulation of plant growth achieved by the present methods can be measured and demonstrated in a number of ways. Stimulation of plant growth can be shown in instances wherein the average height of the plant is increased by at least about 5%, by at least about 10%, by at least about 15% or by at least about 20% as compared to the average height of plants grown under the same conditions but that have not been treated with the bacterial culture or inoculant. Also, stimulation of plant growth can be shown in instances wherein the average leaf diameter of the leaves of plant is increased by at least about 5%, by at least about 10%, by at least about 15% or by at least about 20% as compared to the average leaf diameter of plants grown under the same conditions but that have not been treated with the bacterial culture or inoculant.

The present invention is also directed to plant seeds, which are coated with any of the inoculums or bacteriologically pure bacterial cultures of the present invention. The seed can be from any of the plants discussed in the foregoing sections belonging to monocotyledons, dicotyledons or gymnosperms. The bacterial inoculant or culture can be applied to the seeds through the use of a suitable coating mechanism prior to the seeds being sold into commerce for planting. The process of coating seeds with such an inoculum is generally well known to those skilled in the art. For example, the bacteria can be mixed with a porous, chemically inert granular carrier as described by U.S. Pat. No. 4,875,921, which is incorporated herein by reference with respect to such carriers. Alternatively, the bacterial inoculant can be prepared with or without a carrier and sold as a separate inoculant to be inserted directly into the furrows into which the seed is planted. The process for inserting such inoculants directly into the furrows during seed planting is also generally well known in the art. The density of inoculation of these bacterial cultures onto seeds or into the furrows should be sufficient to populate the sub-soil region adjacent to the roots of the plant with viable bacterial growth.

The present invention also relates to kits for stimulating plant growth, which include an inoculum as described herein, and instructions for applying the inoculum to plants, plant seeds, or a plant growth medium. Kits containing inoculants of the invention will typically include one or more containers of the inoculant, and printed instructions for using the inoculant for promoting plant growth. The kit can also include tools or instruments for reconstituting, measuring, mixing, or applying the inoculant, and will vary in accordance with the particular formulation and intended use of the inoculant.

As shown in Example 10, bacteria provide a good system in which to select mutations for desired characteristics. It is possible to force such mutations through proper selection of desirable traits, while retaining the desired plant growth-promoting capabilities in bacteria. Accordingly, traits that may be desirable to induce in bacterial strains disclosed herein by forcing mutations without affecting plant growth promotion include, but are not limited to, antibiotic resistance, heavy metal resistance, tolerance to heat and cold, high and low salt tolerance, metabolic deficiencies (such as requirements for certain amino acids), metabolic gain-of-function (such as the ability to metabolize polysaccharides or plastic compounds), ability to withstand desiccation, resistance to UV radiation, tolerance of man-made chemicals, ability to bind more tightly to plant roots, higher affinity for plants, increased ability to colonize plants, motility, ability to accept recombinant DNA, and ability to express exogenous proteins. These attributes can be garnered by use of selective pressure or through man-made manipulation of plant growth promoting bacteria's genetics.

Further details concerning the preparation of bacterial inoculants and methods for inoculating plants with bacterial inoculants are found in e.g. U.S. Pat. Nos. 5,586,411; 5,697,186; 5,484,464; 5,906,929; 5,288,296; 4,875,921; 4,828,600; 5,951,978; 5,183,759; 5,041,383; 6,077,505; 5,916,029; 5,360,606; 5,292,507; 5,229,114; 4,421,544; and 4,367,609, each of which is incorporated herein by reference with respect to such methods.

Having described the invention in detail, it will be apparent that modifications and variations are possible without departing from the scope of the invention defined in the appended claims.

EXAMPLES

The following non-limiting examples are provided to further illustrate the present invention.

Example 1

Isolation and Identification of Bacterial Strains

Soil samples from rhizospheres of the healthiest and most resistant potato (*Solanum tuberosum*), yellow summer squash (*Cucurbita pepo*), tomato (*Solanum lycopersicum*), and pole bean (*Phaseolus coccineus*) plants were collected, diluted in sterile water, and spread onto nutrient agar plates. Bacterial isolates that demonstrated high growth rates and were able to be passaged and propagated were selected for further study. The selected strains were grown in minimal media ($KH_2PO_4$ 3 g, $Na_2HPO_4$ 6 g, $NH_4Cl$ 1 g, NaCl 0.50 g, $MgSO_4$ $7H_2O$ 0.15 g, $CaCl_2$ $2H_2O$ 0.013 g, and glucose 1 g, per L dry weight). Overnight cultures (30° C.) of selected strains were spun down, media decanted off, and resuspended in an equal amount of distilled water. Ten lettuce seeds per treatment were planted at a depth of 1 cm in loam top soil (Columbia, Mo.) that was sieved to remove large debris. Seeds were inoculated at planting in 4 cm pots with 0.5 µl of resuspended bacteria in water mixed into 10 ml of $H_2O$. Ten ml of $H_2O$ was sufficient to deliver the bacteria into the 3 $in^3$ (7.62 $cm^3$) of soil as well as saturate the soil for proper germination of seeds. Plants were grown at temperatures between 65-75° F. (18-24° C.) with 11 hours of light/day, and 5 ml of watering every 3 days. After one week, plant heights and leaf diameters, as well as overall health of the plants were collected. Initial screening of rhizosphere isolates resulted in obtaining greater than 200 distinct species of bacteria and fungi from the rhizosphere of the four plants. Some of the bacterial species are described in Table 2. Identified strains are indicated by their proper bacterial identifications. Other strains are indicated by their unknown identification number. Inoculants giving results near control (+/-2%) were left out of the table.

Bacterial strains that produced the greatest effect on the overall plant health and plant height in the initial lettuce trial were subjected to further identification. Bacterial strains were grown overnight in Luria Bertani broth at 37° C., and overnight cultures were spun down in a centrifuge. Media was decanted and the remaining bacterial pellet was subjected to chromosomal DNA isolation using the Qiagen Bacterial Chromosomal DNA Isolation kit. Chromosomal DNA was subjected to PCR amplification of the 16S rRNA coding regions using the primers E338F 5'-ACT CCT ACG GGA GGC AGC AGT-3' (SEQ ID NO: 7), E1099R A 5'-GGG TTG CGC TCG TTG C-3' (SEQ ID NO: 8), and E1099R B 5'-GGG TTG CGC TCG TTA C-3' (SEQ ID NO: 9). PCR amplicons were purified using a Promega PCR purification kit, and the resultant amplicons were diluted and sent to the University of Missouri DNA Core for DNA sequencing. DNA sequences were compared to the NCBI BLAST database of bacterial isolates, and genus and species were identified by direct comparison to known strains. Top identified species are indicated in Table 2. In many cases, 16S rRNA DNA sequences were only able to delineate the genus of the selected bacterial strain. In cases where a direct identification was not forthcoming, additional biochemistry analyses, using methods standard in the field, were performed to differentiate strains at the species and strain levels, and are listed in Table 3.

TABLE 3

| Test | E. cloacae CAP12 | P. kondratiavae NC35 | B. aryabhattai CAP53 | B. flexus BT054 | B. aryabhattai CAP56 | B. sp. BOBA57 |
|---|---|---|---|---|---|---|
| Urease | − | − | − | − | − | + |
| Catalase | + | + | + | + | + | + |
| Oxidase | − | + | + | + | − | − |
| Nitrate | + | + | − | + | − | + |
| Growth, 5% NaCl | + | − | + | + | + | + |
| Growth, 7.5% NaCl | − | − | + | + | + | − |
| Growth, 42° C. | + | + | + | + | + | + |
| Growth, 50° C. | − | − | + | + | + | − |
| Growth, pH 5 | + | − | + | + | + | − |
| Growth, pH 9 | + | + | + | + | + | + |
| Acid, Cellobiose | + | − | + | + | + | − |
| Acid, Lactose | + | − | + | + | − | + |
| Acid, Starch | − | − | − | + | + | − |

TABLE 2

| Bacterial Inoculant | Butterhead Lettuce Avg. Height (cm) | Comparison | SEM |
|---|---|---|---|
| Uninoculated | 1.8 | Control | .07 |
| Paracoccus kondratiavae sp. NC35 | 2 | 111.1% | .05 |
| B. aryabhattai CAP53 | 3.65 | 202.8% | .45 |
| B. flexus BT054 | 2.45 | 136.1% | .11 |
| B. aryabhattai CAP56 | 2.1 | 116.7% | .20 |
| B. nealsonii BOBA57 | 2.8 | 155.6% | .03 |
| E. cloacae CAP12 | 2.4 | 133.3% | .41 |
| Unknown 8 | 1.77 | 77.8% | .65 |
| Unknown 122 | 1.9 | 105.6% | .11 |
| Unknown 15 | 1.4 | 77.8% | .41 |
| Unknown 39 | 1.8 | 100.0% | .20 |
| Unknown 401 | 2 | 111.1% | .21 |
| Unknown 402 | 1.53 | 85.2% | .27 |
| Unknown 41 | 1.45 | 80.6% | .31 |
| Unknown 42 | 1.4 | 77.8% | .15 |
| Unknown 44 | 2.2 | 133.3% | .08 |
| Unknown 51 | 1.83 | 102.9% | .21 |

Example 2

Testing of Bacteria of the Present Invention on Alfalfa

The selected strains were grown in minimal media ($KH_2PO_4$ 3 g, $Na_2HPO_4$ 6 g, $NH_4Cl$ 1 g, NaCl 0.50 g, $MgSO_4$ $7H_2O$ 0.15 g, $CaCl_2$ $2H_2O$ 0.013 g, and glucose 1 g, per L dry weight). Overnight cultures (30° C.) of selected strains were spun down, media decanted off, and bacteria resuspended in an equal amount of distilled water. Ten Zeba-coated alfalfa seeds were planted for each treatment at a depth of 0.6 cm in loam top soil (Columbia, Mo.) that was sieved to remove large debris. Seeds were inoculated at planting with 0.5 µl of resuspended bacteria in water mixed into 10 ml of $H_2O$. Ten ml of $H_2O$ was sufficient to deliver the bacteria into the 3 $in^3$ (7.62 $cm^3$) of soil as well as saturate the soil for proper germination of seeds. Plants were grown at temperatures between 65-75° F. (18-24° C.) with 11 hours of light/day, and 5 ml of watering every 3 days. Alfalfa was allowed to grow for 1 week to analyze emergence and initial outgrowth of plants under described conditions. Identified strains indicated by their proper bacterial identifications and final height data are listed in Table 4.

TABLE 4

| Bacterial Inoculant | Alfalfa Avg. Height (cm) | Comparison | SEM |
|---|---|---|---|
| Uninoculated | 4.82 | — | .008 |
| B. aryabhattai CAP56 | 4.85 | 101.20% | .016 |
| B. nealsonii BOBA57 | 4.86 | 101.70% | .021 |
| E. cloacae CAP12 | 5.6 | 116.23% | .020 |

Example 3

Testing of Bacteria of the Present Invention on Cucumbers

The selected strains were grown in minimal media ($KH_2PO_4$ 3 g, $Na_2HPO_4$ 6 g, $NH_4Cl$ 1 g, NaCl 0.50 g, $MgSO_4$ $7H_2O$ 0.15 g, $CaCl_2$ $2H_2O$ 0.013 g, and glucose 1 g, per L dry weight). Overnight cultures (30° C.) of selected strains were spun down, media decanted off, and resuspended in equal amount of distilled water. Ten cucumber seeds were planted for each treatment at a depth of 1 cm in loam top soil (Columbia, Mo.) that was sieved to remove large debris. Seeds were inoculated at planting with 0.5 µl of resuspended bacteria in water mixed into 10 ml of $H_2O$. Ten ml of $H_2O$ was sufficient to deliver the bacteria into the 3 in$^3$ (7.62 cm$^3$) of soil as well as saturate the soil for proper germination of seeds. Plants were grown at temperatures between 65-75° F. (18-24° C.) with 11 hours of light/day, and 5 ml of watering every 3 days. Cucumbers were allowed to grow for 2 weeks to analyze emergence and initial outgrowth of plants under described conditions. Identified strains indicated by their proper bacterial identifications and final height data are listed in Table 5.

TABLE 5

| Bacterial Inoculant | Cucumbers Avg. Height (cm) | Comparison | SEM |
|---|---|---|---|
| Uninoculated | 11.23 | — | .067 |
| B. aryabhattai CAP53 | 11.5 | 102.00% | .023 |
| B. aryabhattai CAP56 | 11.35 | 101.20% | .035 |
| B. nealsonii BOBA57 | 11.33 | 101.10% | .014 |

Example 4

Testing of Bacteria of the Present Invention on Yellow Squash

The selected strains were grown in minimal media ($KH_2PO_4$ 3 g, $Na_2HPO_4$ 6 g, $NH_4Cl$ 1 g, NaCl 0.50 g, $MgSO_4$ $7H_2O$ 0.15 g, $CaCl_2$ $2H_2O$ 0.013 g, and glucose 1 g, per L dry weight). Overnight cultures (30° C.) of selected strains were spun down, media decanted off, and resuspended in an equal amount of distilled water. Ten yellow squash seeds were planted for each treatment at a depth of 1 cm in loam top soil (Columbia, Mo.) that was sieved to remove large debris. Seeds were inoculated at planting with 0.5 µl of resuspended bacteria in water mixed into 10 ml of $H_2O$. Ten ml of $H_2O$ was sufficient to deliver the bacteria into the 3 in$^3$ (7.62 cm$^3$) of soil as well as saturate the soil for proper germination of seeds. Plants were grown at temperatures between 65-75° F. (18-24° C.) with 11 hours of light/day, and 5 ml of watering every 3 days. Squash was allowed to grow for 2 weeks to analyze emergence and initial outgrowth of plants under described conditions. Identified strains indicated by their proper bacterial identifications, final height data, and final leaf diameter data are listed in Table 6.

TABLE 6

| Bacterial Inoculant | Avg. Height (cm) | Yellow Squash Comparison | SEM | Leaf Diameter (cm) | Comparison |
|---|---|---|---|---|---|
| Uninoculated | 10.16 | — | .028 | 5.08 | — |
| B. aryabhattai CAP53 | 11.75 | 115.60% | .055 | 7.25 | 142.60% |
| B. flexus BT054 | 11.88 | 116.90% | .017 | 6.36 | 125.20% |
| B. aryabhattai CAP56 | 11.95 | 117.60% | .027 | 6.33 | 124.60% |
| B. nealsonii BOBA57 | 11.89 | 117.00% | .118 | 6.42 | 126.40% |
| E. cloacae CAP12 | 11.42 | 112.30% | .039 | 6.83 | 134.40% |

Example 5

Testing of Bacteria of the Present Invention on Ryegrass

The selected strains were grown in minimal media ($KH_2PO_4$ 3 g, $Na_2HPO_4$ 6 g, $NH_4Cl$ 1 g, NaCl 0.50 g, $MgSO_4$ $7H_2O$ 0.15 g, $CaCl_2$ $2H_2O$ 0.013 g, and glucose 1 g, per L dry weight). Overnight cultures (30° C.) of selected strains were spun down, media decanted off, and resuspended in an equal amount of distilled water. Thirty ryegrass seeds were planted for each treatment at a depth of 0.3 cm in loam top soil (Columbia, Mo.) that was sieved to remove large debris. Seeds were inoculated at planting with 0.5 µl of resuspended bacteria in water mixed into 10 ml of $H_2O$. Ten ml of $H_2O$ was sufficient to deliver the bacteria into the 3 in$^3$ (7.62 cm$^3$) of soil as well as saturate the soil for proper germination of seeds. Plants were grown at temperatures between 65-75° F. (18-24° C.) with 11 hours of light/day, and 5 ml of watering every 3 days. Ryegrass was allowed to grow for 1.5 weeks to analyze emergence and initial outgrowth of plants under described conditions. Identified strains indicated by their proper bacterial identifications and height data are listed in Table 7.

TABLE 7

| Bacterial Inoculant | Ryegrass Avg. Height (cm) | Comparison | SEM |
|---|---|---|---|
| Uninoculated | 1.61 | — | .023 |
| B. aryabhattai CAP53 | 2.01 | 124.70% | .012 |
| B. flexus BT054 | 2.21 | 137.30% | .034 |
| B. aryabhattai CAP56 | 2.19 | 136.00% | .009 |
| B. nealsonii BOBA57 | 2.29 | 142.40% | .045 |
| E. cloacae CAP12 | 1.98 | 122.50% | .015 |

Example 6

Testing of Bacteria of the Present Invention on Corn

The selected strains were grown in minimal media ($KH_2PO_4$ 3 g, $Na_2HPO_4$ 6 g, $NH_4Cl$ 1 g, NaCl 0.50 g, $MgSO_4$ $7H_2O$ 0.15 g, $CaCl_2$ $2H_2O$ 0.013 g, and glucose 1 g, per L dry weight). Overnight cultures (30° C.) of selected strains were spun down, media decanted off, and resuspended in an equal amount of distilled water. Ten corn seeds were planted for each treatment at a depth of 2.5 cm in loam top soil (Columbia, Mo.) that was sieved to remove large debris. Seeds were inoculated at planting with 0.5 µl of resuspended bacteria in water mixed into 10 ml of $H_2O$. Ten ml of $H_2O$ was sufficient to deliver the bacteria into the 3 in$^3$ (7.62 cm$^3$) of soil as well as saturate the soil for proper germination of seeds. Plants were grown at temperatures between 65-75° F. (18-24° C.) with 11 hours of light/day, and 5 ml of watering every 3 days. Corn was allowed to grow for 2 weeks to analyze emergence and initial outgrowth of plants under described conditions. Identified strains indicated by their proper bacterial identifications and final height data are listed in Table 8.

TABLE 8

| Bacterial Inoculant | Corn Avg. Height (cm) | Comparison | SEM |
| --- | --- | --- | --- |
| Uninoculated | 8.9 | — | .039 |
| B. aryabhattai CAP53 | 11.01 | 123.60% | .081 |
| B. flexus BT054 | 9.96 | 112.00% | .095 |
| B. aryabhattai CAP56 | 9.54 | 107.10% | .088 |
| B. nealsonii BOBA57 | 9.23 | 103.70% | .077 |

Example 7

Testing of Bacteria on Soybeans

The selected strains were grown in minimal media ($KH_2PO_4$ 3 g, $Na_2HPO_4$ 6 g, $NH_4Cl$ 1 g, NaCl 0.50 g, $MgSO_4$ $7H_2O$ 0.15 g, $CaCl_2$ $2H_2O$ 0.013 g, and glucose 1 g, per L dry weight, or for Bradyrhizobium or Rhizobium on yeast mannitol media). Overnight cultures (30° C.) of selected strains were spun down, media decanted off, and resuspended in equal amount of distilled water. Ten soybean seeds were planted for each treatment at a depth of 2.5 cm in loam top soil (Columbia, Mo.) that was sieved to remove large debris. Seeds were inoculated at planting with 0.5 µl of resuspended bacteria in water mixed into 10 ml of $H_2O$. When testing two bacterial strains, 0.5 µl of each resuspended bacteria was mixed into 10 ml of $H_2O$. Ten ml of $H_2O$ was sufficient to deliver the bacteria into the 3 in$^3$ (7.62 cm$^3$) of soil as well as saturate the soil for proper germination of seeds. Plants were grown at temperatures between 65-75° F. (18-24° C.) with 11 hours of light/day, and 5 ml of watering every 3 days. Soybeans were allowed to grow for 2 weeks to analyze emergence and initial outgrowth of plants under described conditions. Identified strains indicated by their proper bacterial identifications and final height data are listed in Table 9. Co-inoculation of bacteria strains in the present invention with members of the Bradyrhizobium sp. or Rhizobium sp. lead to an increase in plant growth compared to either inoculant alone.

TABLE 9

| Bacterial Inoculant | Soybeans Avg. Height (cm) | Comparison | SEM |
| --- | --- | --- | --- |
| Uninoculated | 13.94 | — | .089 |
| B. aryabhattai CAP53 | 16.32 | 117.1% | .146 |
| B. flexus BT054 | 17.85 | 128.0% | .177 |
| B. aryabhattai CAP56 | 17.23 | 123.6% | .133 |
| B. aryabhattai CAP53 | 16.32 | 117.1% | .077 |
| B. aryabhattai CAP53 and Bradyrhizobium sp. | 16.72 | 119.9% | .182 |
| B. aryabhattai CAP53 and Rhizobium sp. | 17.32 | 124.2% | .086 |

TABLE 9-continued

| Bacterial Inoculant | Soybeans Avg. Height (cm) | Comparison | SEM |
| --- | --- | --- | --- |
| Bradyrhizobium sp. | 14.25 | 102.2% | |
| Rhizobium sp. | 14.75 | 105.8% | |

Example 8

Testing of Bacteria of the Present Invention on Soybeans with the Additive Effect of Plant-Growth-Promoting Chemicals The selected strains were grown in minimal media ($KH_2PO_4$ 3 g, $Na_2HPO_4$ 6 g, $NH_4Cl$ 1 g, NaCl 0.50 g, $MgSO_4$ $7H_2O$ 0.15 g, $CaCl_2$ $2H_2O$ 0.013 g, and glucose 1 g, per L dry weight). Overnight cultures (30° C.) of selected strains were spun down, media decanted off, and resuspended in equal amount of distilled water. Ten soybean seeds were planted for each treatment at a depth of 2.5 cm in loam top soil (Columbia, Mo.) that was sieved to remove large debris. Seeds were inoculated at planting with 0.5 µl of resuspended bacteria in water mixed into 10 ml of $H_2O$ alone, into 10 ml of $H_2O$ with 0.5 µl glycerol, into 10 ml of $H_2O$ with 0.5 µl 2,3-butanediol, or into 10 ml of $H_2O$ with 0.5 mg yeast extract. Ten ml of $H_2O$ was sufficient to deliver the bacteria into the 3 in$^3$ (7.62 cm$^3$) of soil as well as saturate the soil for proper germination of seeds. Plants were grown at temperatures between 65-75° F. (18-24° C.) with 11 hours of light/day, and 5 ml of watering every 3 days. Soybeans were allowed to grow for 2 weeks to analyze emergence and initial outgrowth of plants under described conditions. Identified strains indicated by their proper bacterial identifications and final height data are listed in Table 10.

TABLE 10

| Bacterial Inoculant | Soybeans Avg. Height (cm) | Comparison to Uninoculated | Comparison to Inoculant | SEM |
| --- | --- | --- | --- | --- |
| Uninoculated | 11.24 | — | | .153 |
| Uninoculated and Glycerol | 12.34 | 109.8% | | .107 |
| Uninoculated and Yeast Extract | 14.03 | 124.8% | | .212 |
| B. aryabhattai CAP53 | 12.56 | 111.7% | — | .146 |
| B. aryabhattai CAP53 and Glycerol | 13.22 | 117.6% | 105.3% | .118 |
| B. aryabhattai CAP53 and Yeast Extract | 14.73 | 131.0% | 117.3% | .119 |
| Paracoccus sp. NC35 | 13.32 | 118.5% | — | .027 |
| Paracoccus sp. NC35 and 2,3-butanediol | 15.09 | 134.3% | 113.3% | .210 |
| Paracoccus sp. NC35 and Yeast Extract | 15.83 | 140.8% | 118.8% | .145 |

Example 9

Testing of Bacteria of the Present Invention on Corn with the Additive Effect of Plant-Growth-Promoting Chemicals The selected strains were grown in minimal media ($KH_2PO_4$ 3 g, $Na_2HPO_4$ 6 g, $NH_4Cl$ 1 g, NaCl 0.50 g, $MgSO_4$ $7H_2O$ 0.15 g, $CaCl_2$ $2H_2O$ 0.013 g, and glucose 1 g, per L dry weight). Overnight cultures (30° C.) of selected strains were spun down, media decanted off, and resuspended in an equal amount of distilled water. Ten corn seeds were planted for each treatment at a depth of 2.5 cm in loam top soil (Columbia, Mo.) that was sieved to remove large debris. Seeds were inoculated at planting with 0.5 µl of resuspended bacteria in water mixed into 10 ml of $H_2O$ alone, into 10 ml of $H_2O$ with 0.5 µl 2,3-butanediol, or into 10 ml of $H_2O$ with 0.5 mg yeast extract. Ten ml of $H_2O$ was sufficient to deliver the bacteria into the 3 in$^3$ (7.62 cm$^3$) of soil as well as saturate the soil for proper germination of seeds. Plants were grown at temperatures between 65-75° F. (18-24° C.) with 11 hours of light/day, and 5 ml of watering every 3 days. Corn was allowed to grow for 2 weeks to analyze emergence and initial outgrowth of plants under described conditions. Identified strains indicated by their proper bacterial identifications and final height data are listed in Table 11.

TABLE 11

| Bacterial Inoculant | Corn Avg. Height (cm) | Comparison to Uninoculated | Comparison to Inoculant | SEM |
|---|---|---|---|---|
| Uninoculated | 15.15 | — | | .156 |
| Uninoculated and 2,3-butanediol | 16.03 | 105.8% | | .078 |
| Uninoculated and Yeast Extract | 17.04 | 112.5% | | .101 |
| *Paracoccus* sp. NC35 | 16.04 | 105.9% | — | .023 |
| *Paracoccus* sp. NC35 and 2,3-butanediol | 16.24 | 107.2% | 101.2% | .111 |
| *Paracoccus* sp. NC35 and Yeast Extract | 17.96 | 118.5% | 112.0% | .127 |

Example 10

Generation of Mutants Able to Grow in High Salt Conditions that Retain Plant Growth-Promoting Ability Using Selective Pressure

*Paracoccus* sp. NC35 and was found to be salt sensitive and not very active in high salt soil types (Table 3). To induce salt tolerance in these plant growth promoting bacteria, a selective pressure using successively higher concentrations of NaCl was used to find mutants that could tolerate these high salt soil types. The selected strains were grown in Luria Bertani liquid media at 37° C. overnight and plated on 1% NaCl salt agar media and allowed to grow for 48 hours at 30° C. Individual colonies of strains that survived on the 1% salt LB agar plates were grown in Luria Bertani with 1% NaCl liquid media at 37° C. overnight and plated on 3% NaCl salt LB agar media for 48 hours at 30° C. Colonies of strains that survived on the 3% NaCl salt LB agar were grown in Luria Bertani with 3% NaCl liquid media at 37° C. overnight and plated on 5% NaCl salt LB agar media and allowed to grow for 48 hours at 30° C. Bacterial colonies selected from the 5% salt LB agar plates were grown in Luria Bertani overnight plus 5% NaCl media at 37° C. Overnight cultures of original strains in minimal media and salt tolerant mutants were grown overnight and were spun down, media decanted off, and resuspended in equal amount of distilled water. Nine soybean seeds were planted for each treatment at a depth of 2.5 cm in loam top soil (Columbia, Mo.) or salt loam with 5% salt (w/w) that was sieved to remove large debris. Seeds were inoculated at planting with 0.5 µl of resuspended bacteria in water mixed into 10 ml of $H_2O$. Ten ml of $H_2O$ was sufficient to deliver the bacteria into the 3 in$^3$ (7.62 cm$^3$) of soil as well as saturate the soil for proper germination of seeds. Plants were grown at temperatures between 65-75° F. (18-24° C.) with 11 hours of light/day, and 5 ml of watering every 3 days. Soybeans were allowed to grow for 2 weeks to analyze emergence and initial outgrowth of plants under described conditions. Identified strains indicated by their proper bacterial identifications and final height data are listed in Table 12. Mutations were forced in a salt-sensitive strain that retained plant growth-promoting ability. The *Paracoccus* sp. NC35 salt tolerant strain was deposited with the United States Department of Agriculture (USDA) Agricultural Research Service (ARS), having the address 1815 North University Street, Peoria, Ill. 61604 U.S.A., on Mar. 17, 2014, and assigned the accession number NRRL B-50948.

TABLE 12

| Bacterial Inoculant | Avg. Height, Loam Soil (cm) | Percentage | Avg. height, 5% Salt Soil (cm) | Percentage | SEM, Loam Soil | SEM, 5% Salt Soil |
|---|---|---|---|---|---|---|
| $H_2O$ Control | 10.54 | 100% | 7.34 | 100% | .322 | .117 |
| *Paracoccus* sp NC35, salt sensitive | 11.91 | 113% | 7.15 | 97.4% | .115 | .215 |
| *Paracoccus* sp. NC35 salt tolerant | 12.02 | 114% | 9.23 | 125.7% | .451 | .105 |

When introducing elements of the present invention, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above products and methods without departing from the scope of the invention, it is intended that all matter contained in the above description shall be interpreted as illustrative and not in a limiting sense.

What is claimed is:

1. A method for stimulating plant growth, comprising applying a bacterial culture to a plant, plant seed, or plant growth medium,
   wherein the bacteria in the bacterial culture comprises:
   (a) *Bacillus aryabhattai* strain CAP53 (NRRL No. B-50819);
   (b) *Bacillus aryabhattai* strain CAP56 (NRRL No. B-50817);
   (c) *Bacillus flexus* strain BT054 (NRRL No. B-50816);
   (d) *Paracoccus kondratievae* strain NC35 (NRRL No. B-50820);
   (e) *Enterobacter cloacae* strain CAP12 (NRRL No. B-50822);
   (f) *Bacillus nealsonii* strain BOBA57 (NRRL No. B-50821); or
   a mutant having all of the identifying characteristics of any one of said strains, wherein the mutant comprises one or more mutations and retains the ability to promote plant growth; and
   the bacterial culture is applied in an inoculum comprising an effective amount of the bacterial culture and an agriculturally acceptable carrier.

2. The method of claim 1 wherein the inoculum comprises an effective amount of a mixture comprising at least two of the bacterial cultures of claim 1.

3. The method of claim 1, wherein the inoculum further comprises an effective amount of a rhizobacteria.

4. The method of claim 3, wherein the rhizobacteria comprises *Bradyrhizobium* genus bacteria, *Rhizobium* genus bacteria, or a combination thereof.

5. The method of claim 4, wherein the *Bradyrhizobium* genus bacteria comprises *Bradyrhizobium japonicum*.

6. The method of claim 4, wherein the *Rhizobium* genus bacteria comprises *Rhizobium phaseoli*, *Rhizobium leguminosarum*, or a combination thereof.

7. The method of claim 1, wherein the agriculturally acceptable carrier comprises a dispersant, a surfactant, an additive, water, a thickener, an anticaking agent, residue breakdown, a composting formulation, a granular application, diatomaceous earth, an oil, a coloring agent, a stabilizer, a preservative, a polymer, a coating, or a combination thereof.

8. The method of claim 1, wherein the agriculturally acceptable carrier comprises vermiculite, charcoal, sugar factory carbonation press mud, rice husk, carboxymethyl cellulose, peat, perlite, fine sand, calcium carbonate, flour, alum, a starch, talc, polyvinyl pyrrolidone, or a combination thereof.

9. The method of claim 1, wherein the inoculum is formulated as a seed coating formulation, a liquid formulation for application to plants or to a plant growth medium, or a solid formulation for application to the plants or to the plant growth medium.

10. The method of claim 9, wherein the seed coating formulation is an aqueous or oil-based solution for application to seeds.

11. The method of claim 9, wherein the seed coating formulation is a powder or granular formulation for application to seeds.

12. The method of claim 9, wherein the liquid formulation for application to the plants or to the plant growth medium is in a concentrated formulation or a working form formulation.

13. The method of claim 9, wherein the solid formulation for application to the plants or to the plant growth medium is a granular formulation or a powder agent.

14. The method of claim 1, wherein the inoculum further comprises a fertilizer, a micronutrient fertilizer material, an insecticide, a herbicide, a plant growth amendment, a fungicide, a molluscicide, an algicide, a bacterial inoculant, a fungal inoculant, or a combination thereof.

15. The method of claim 14, wherein the bacterial inoculant comprises a bacterial inoculant of the genus *Rhizobium*, a bacterial inoculant of the genus *Bradyrhizobium*, a bacterial inoculant of the genus *Mesorhizobium*, a bacterial inoculant of the genus *Azorhizobium*, a bacterial inoculant of the genus *Allorhizobium*, a bacterial inoculant of the genus *Sinorhizobium*, a bacterial inoculant of the genus *Kluyvera*, a bacterial inoculant of the genus *Azotobacter*, a bacterial inoculant of the genus *Pseudomonas*, a bacterial inoculant of the genus *Azospirillium*, a bacterial inoculant of the genus *Bacillus*, a bacterial inoculant of the genus *Streptomyces*, a bacterial inoculant of the genus *Paenibacillus*, a bacterial inoculant of the genus *Paracoccus*, a bacterial inoculant of the genus *Enterobacter*, a bacterial inoculant of the genus *Alcaligenes*, a bacterial inoculant of the genus *Mycobacterium*, a bacterial inoculant of the genus *Trichoderma*, a bacterial inoculant of the genus *Gliocladium*, a bacterial inoculant of the genus *Glomus*, a bacterial inoculant of the genus *Klebsiella*, or a combination thereof.

16. The method of claim 14, wherein the insecticide comprises an organophosphate, a carbamate, a pyrethroid, an acaricide, an alkyl phthalate, boric acid, a borate, a fluoride, sulfur, a haloaromatic substituted urea, a hydrocarbon ester, a biologically-based insecticide, or a combination thereof.

17. The method of claim 14, wherein the fungicide comprises a substituted benzene, a thiocarbamate, an ethylene bis dithiocarbamate, a thiophthalidamide, a copper compound, an organomercury compound, an organotin compound, a cadmium compound, anilazine, benomyl, cyclohexamide, dodine, etridiazole, iprodione, metlaxyl, thiamimefon, triforine, or a combination thereof.

18. The method of claim 1, comprising applying the bacterial culture to a plant seed.

19. The method of claim 1, wherein the bacteria in the bacterial culture is *Paracoccus kondratievae* strain NC35 and the bacteria has a 16S ribosomal RNA sequence having at least about 98%, at least about 99%, or 100% sequence identity with the sequence of SEQ ID NO: 4.

* * * * *

SEQUENCE LISTING

<160> NUMBER OF SEQ ID NOS: 9

<210> SEQ ID NO 1
<211> LENGTH: 717
<212> TYPE: DNA
<213> ORGANISM: Bacillus aryabhattai
<220> FEATURE:
<221> NAME/KEY: misc_feature
<222> LOCATION: (3)..(4)

<223> OTHER INFORMATION: n = a, c, g, or t

<400> SEQUENCE: 1

```
ggnncaacgc cgcgtgagtg atgaaggctt tcgggtcgta aaactctgtt gttagggaag      60
aacaagtacg agagtaactg ctcgtacctt gacggtacct aaccagaaag ccacggctaa     120
ctacgtgcca gcagccgcgg taatacgtag gtggcaagcg ttatccggaa ttattgggcg     180
taaagcgcgc gcaggcggtt tcttaagtct gatgtgaaag cccacggctc aaccgtggag     240
ggtcattgga aactggggaa cttgagtgca gaagagaaaa gcggaattcc acgtgtagcg     300
gtgaaatgcg tagagatgtg gaggaacacc agtggcgaag cggcttttt ggtctgtaac     360
tgacgctgag gcgcgaaagc gtggggagca acaggatta gatacctgg tagtccacgc      420
cgtaaacgat gagtgctaag tgttagaggg tttccgccct ttagtgctgc agctaacgca     480
ttaagcactc cgcctgggga gtacggtcgc aagactgaaa ctcaaaggaa ttgacggggg     540
cccgcacaag cggtggagca tgtggtttaa ttcgaagcaa cgcgaagaac cttaccaggt     600
cttgacatcc tctgacaact ctagagatag agcgttcccc ttcggggac agagtgacag      660
gtggtgcatg gttgtcgtca gctcgtgtcg tgagatgttg ggttaagtcc cgcaacg       717
```

<210> SEQ ID NO 2
<211> LENGTH: 718
<212> TYPE: DNA
<213> ORGANISM: Bacillus aryabhattai
<220> FEATURE:
<221> NAME/KEY: misc_feature
<222> LOCATION: (6)..(6)
<223> OTHER INFORMATION: n = a, c, g, or t
<220> FEATURE:
<221> NAME/KEY: misc_feature
<222> LOCATION: (9)..(10)
<223> OTHER INFORMATION: n = a, c, g, or t

<400> SEQUENCE: 2

```
tctganggnn cacgccgcgt gagtgatgaa ggctttcggg tcgtaaaact ctgttgttag      60
ggaagaacaa gtacgagagt aactgctcgt accttgacgg tacctaacca gaaagccacg     120
gctaactacg tgccagcagc cgcggtaata cgtaggtggc aagcgttatc cggaattatt     180
gggcgtaaag cgcgcgcagg cggtttctta agtctgatgt gaaagcccac ggctcaaccg     240
tggagggtca ttggaaactg ggaacttga gtgcagaaga gaaaagcgga attccacgtg     300
tagcggtgaa atgcgtagag atgtggagga acaccagtgg cgaaggcggc ttttggtct    360
gtaactgacg ctgaggcgcg aaagcgtggg gagcaaacag gattagatac cctggtagtc     420
cacgccgtaa acgatgagtg ctaagtgtta gagggtttcc gcccttagt gctgcagcta    480
acgcattaag cactccgcct ggggagtacg gtcgcaagac tgaaactcaa aggaattgac     540
gggggcccgc acaagcggtg gagcatgtgg tttaattcga agcaacgcga gaaccttac     600
caggtcttga catcctctga caactctaga gatagagcgt tccccttcgg gggacagagt     660
gacaggtggt gcatggttgt cgtcagctcg tgtcgtgaga tgttgggtta agtcccgc      718
```

<210> SEQ ID NO 3
<211> LENGTH: 716
<212> TYPE: DNA
<213> ORGANISM: Bacillus flexus
<220> FEATURE:
<221> NAME/KEY: misc_feature
<222> LOCATION: (4)..(4)
<223> OTHER INFORMATION: n = a, c, g, or t
<220> FEATURE:
<221> NAME/KEY: misc_feature
<222> LOCATION: (22)..(22)
<223> OTHER INFORMATION: n = a, c, g, or t

<400> SEQUENCE: 3

```
ggancaacgc cgcgtgagtg angaaggctt tcgggtcgta aaactctgtt gttagggaag      60
aacaagtaca agagtaactg cttgtaccct gacggtacct aaccagaaag ccacggctaa     120
ctacgtgcca gcagccgcgg taatacgtag gtggcaagcg ttatccggaa ttattgggcg     180
taaagcgcgc gcaggcggtt tcttaagtct gatgtgaaag cccacggctc aaccgtggag     240
ggtcattgga aactggggaa cttgagtgca gaagagaaaa gcggaattcc acgtgtagcg     300
gtgaaatgcg tagagatgtg gaggaacacc agtggcgaag gcggcttttt ggtctgtaac     360
tgacgctgag gcgcgaaagc gtggggagca acaggatta gataccctgg tagtccacgc     420
cgtaaacgat gagtgctaag tgttagaggg tttccgccct ttagtgctgc agctaacgca     480
ttaagcactc cgcctgggga gtacggtcgc aagactgaaa ctcaaaggaa ttgacggggg     540
cccgcacaag cggtggagca tgtggtttaa ttcgaagcaa cgcgaagaac cttaccaggt     600
cttgacatcc tctgacaact ctagagatag agcgttcccc ttcggggac agagtgacag     660 gtggtgcatg gttgtcgtca gctcgtgtcg tgagatgttg ggttaagtcc cgcaac        716
```

<210> SEQ ID NO 4
<211> LENGTH: 676
<212> TYPE: DNA
<213> ORGANISM: Paracoccus kondratievae
<220> FEATURE:
<221> NAME/KEY: misc_feature
<222> LOCATION: (13)..(15)
<223> OTHER INFORMATION: n = a, c, g, or t
<220> FEATURE:
<221> NAME/KEY: misc_feature
<222> LOCATION: (19)..(19)
<223> OTHER INFORMATION: n = a, c, g, or t
<220> FEATURE:
<221> NAME/KEY: misc_feature
<222> LOCATION: (44)..(44)
<223> OTHER INFORMATION: n = a, c, g, or t

<400> SEQUENCE: 4

```
gccgcgtgag tgnnnaagnc cctagggttg taaagctctt tcanctggga agataatgac      60
tgtaccagca gaagaagccc cggctaactc cgtgccagca gccgcggtaa tacggagggg     120
gctagcgttg ttcggaatta ctgggcgtaa agcgcacgta ggcggaccgg aaagttgggg     180
gtgaaatccc ggggctcaac cccggaactg ccttcaaaac tatcggtctg gagttcgaga     240
gaggtgagtg gaattccgag tgtagaggtg aaattcgtag atattcggag gaacaccagt     300
ggcgaaggcg gctcactggc tcgatactga cgctgaggtg cgaaagcgtg gggagcaaac     360
aggattagat accctggtag tccacgccgt aaacgatgaa tgccagtcgt cgggcagcat     420
gctgttcggt gacacaccta acggattaag cattccgcct ggggagtacg gtcgcaagat     480
taaaactcaa aggaattgac ggggggcccgc acaagcggtg gagcatgtgg tttaattcga     540
agcaacgcgc agaaccttac caaccccttga catcccagga cagcccgaga gatcgggtct     600
ccacttcggt ggcctggaga caggtgctgc atggctgtcg tcagctcgtg tcgtgagatg     660
ttcggttaag tccggc                                                    676
```

<210> SEQ ID NO 5
<211> LENGTH: 728
<212> TYPE: DNA
<213> ORGANISM: Enterobacter cloacae
<220> FEATURE:

```
<221> NAME/KEY: misc_feature
<222> LOCATION: (4)..(5)
<223> OTHER INFORMATION: n = a, c, g, or t
<220> FEATURE:
<221> NAME/KEY: misc_feature
<222> LOCATION: (12)..(12)
<223> OTHER INFORMATION: n = a, c, g, or t
<220> FEATURE:
<221> NAME/KEY: misc_feature
<222> LOCATION: (33)..(33)
<223> OTHER INFORMATION: n = a, c, g, or t
<220> FEATURE:
<221> NAME/KEY: misc_feature
<222> LOCATION: (719)..(719)
<223> OTHER INFORMATION: n = a, c, g, or t
<220> FEATURE:
<221> NAME/KEY: misc_feature
<222> LOCATION: (721)..(722)
<223> OTHER INFORMATION: n = a, c, g, or t

<400> SEQUENCE: 5
ctgnnncagc cntgccgcgt gtatgaagaa ggncttcggg ttgtaaagta ctttcagcgg      60
ggaggaaggt gttgtggtta ataaccacag caattgacgt tacccgcaga agaagcaccg     120
gctaactccg tgccagcagc cgcggtaata cggagggtgc aagcgttaat cggaattact     180
gggcgtaaag cgcacgcagg cggtctgtca gtcggatgt gaaatcccccg gctcaacct     240
gggaactgca ttcgaaactg gcaggctaga gtcttgtaga gggggtaga attccaggtg     300
tagcggtgaa atgcgtagag atctggagga ataccggtgg cgaaggcggc ccctggaca     360
aagactgacg ctcaggtgcg aaagcgtggg gagcaaacag gattagatac cctggtagtc    420
cacgccgtaa acgatgtcga tttggaggtt gtgcccttga ggcgtggctt ccggagctaa    480
cgcgttaaat cgaccgcctg ggagtacgg ccgcaaggtt aaaactcaaa tgaattgacg    540
ggggcccgca caagcggtgg agcatgtggt ttaattcgat gcaacgcgaa gaaccttacc    600
tggtcttgac atccacagaa ctttccagag atggattggt gccttcggga actgtgagac    660
aggtgctgca tggctgtcgt cagctcgtgt tgtgaaatgt tgggttaagt cccgcaacna    720
nncgcaac                                                            728

<210> SEQ ID NO 6
<211> LENGTH: 717
<212> TYPE: DNA
<213> ORGANISM: Bacillus nealsonii
<220> FEATURE:
<221> NAME/KEY: misc_feature
<222> LOCATION: (3)..(4)
<223> OTHER INFORMATION: n = a, c, g, or t
<220> FEATURE:
<221> NAME/KEY: misc_feature
<222> LOCATION: (8)..(8)
<223> OTHER INFORMATION: n = a, c, g, or t

<400> SEQUENCE: 6
tgnngganca acgccgcgtg agtgatgaag gttttcggat cgtaaaactc tgttgttagg      60
gaagaacaag tacgagagta actgctcgta ccttgacggt acctaaccag aaagccacgg    120
ctaactacgt gccagcagcc gcggtaatac gtaggtggca agcgttgtcc ggaattattg    180
ggcgtaaagc gcgcgcaggc ggtccttta gtctgatgtg aaagcccacg gctcaaccgt    240
ggagggtcat tggaaactgg gggacttgag tgcagaagag aagagtggaa ttccacgtgt    300
agcggtgaaa tgcgtagaga tgtggaggaa caccagtggc gaaggcgact ctttggtctg    360
taactgacgc tgaggcgcga aagcgtgggg agcaaacagg attagatacc ctggtagtcc    420
acgccgtaaa cgatgagtgc taagtgttag agggtttccg ccccttttagtg ctgcagcaaa    480
```

```
cgcattaagc actccgcctg gggagtacgg ccgcaaggct gaaactcaaa ggaattgacg    540
ggggcccgca caagcggtgg agcatgtggt ttaattcgaa gcaacgcgaa gaaccttacc    600
aggtcttgac atctcctgac aatcctagag ataggacgtt cccttcggg ggacaggatg    660 acaggtggtg catggttgtc gtcagctcgt gtcgtgagat gttgggttaa gtcccgc      717

<210> SEQ ID NO 7
<211> LENGTH: 21
<212> TYPE: DNA
<213> ORGANISM: Artificial sequence
<220> FEATURE:
<223> OTHER INFORMATION: Primer

<400> SEQUENCE: 7
actcctacgg gaggcagcag t                                              21

<210> SEQ ID NO 8
<211> LENGTH: 16
<212> TYPE: DNA
<213> ORGANISM: Artificial sequence
<220> FEATURE:
<223> OTHER INFORMATION: Primer

<400> SEQUENCE: 8
gggttgcgct cgttgc                                                    16

<210> SEQ ID NO 9
<211> LENGTH: 16
<212> TYPE: DNA
<213> ORGANISM: Artificial sequence
<220> FEATURE:
<223> OTHER INFORMATION: Primer

<400> SEQUENCE: 9
gggttgcgct cgttac                                                    16
```